United States Patent
Van Liere et al.

(10) Patent No.: US 12,426,860 B2
(45) Date of Patent: Sep. 30, 2025

(54) DUAL LUMEN COAXIAL INTRODUCER HAVING INTEGRATED TISSUE MARKER DELIVERY

(71) Applicant: C. R. Bard, Inc., Franklin Lakes, NJ (US)

(72) Inventors: Chad Van Liere, Phoenix, AZ (US); Angela K. Jensen, Phoenix, AZ (US); Channing M. Hughes, Colorado Springs, CO (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 1343 days.

(21) Appl. No.: 17/042,533

(22) PCT Filed: Apr. 18, 2018

(86) PCT No.: PCT/US2018/028145
§ 371 (c)(1),
(2) Date: Sep. 28, 2020

(87) PCT Pub. No.: WO2019/203820
PCT Pub. Date: Oct. 24, 2019

(65) Prior Publication Data
US 2021/0030404 A1     Feb. 4, 2021

(51) Int. Cl.
*A61B 10/02*    (2006.01)
*A61B 17/34*    (2006.01)
*A61B 90/00*    (2016.01)

(52) U.S. Cl.
CPC ...... *A61B 10/0275* (2013.01); *A61B 17/3403* (2013.01); *A61B 17/3421* (2013.01);
(Continued)

(58) Field of Classification Search
None
See application file for complete search history.

(56) References Cited

U.S. PATENT DOCUMENTS

| | | | |
|---|---|---|---|
| 5,775,333 A | 7/1998 | Burbank et al. | |
| 5,782,775 A | 7/1998 | Milliman et al. | |

(Continued)

FOREIGN PATENT DOCUMENTS

| | | |
|---|---|---|
| WO | 2007008829 A2 | 1/2007 |
| WO | 2009009274 A2 | 1/2009 |

(Continued)

OTHER PUBLICATIONS

Office Action dated Mar. 3, 2022, pertaining to Japanese Patent Application 2020-557187 (translation).

*Primary Examiner* — Tse W Chen
*Assistant Examiner* — Martin Nathan Ortega
(74) *Attorney, Agent, or Firm* — Dinsmore & Shohl, LLC

(57) ABSTRACT

A dual lumen coaxial introducer, for use with an elongate needle, includes a hub, an elongate member, and a pushrod. The elongate member has a first lumen, a second lumen, a proximal end portion, and a distal end. The proximal end portion is fixedly attached to the hub. The first lumen of the elongate member defines a longitudinal axis and is configured to slidably receive the elongate needle. The pushrod is located in the second lumen of the elongate member. The pushrod has a distal end surface. The pushrod is movable in the second lumen between a retracted position and an extended position. In the retracted position, the distal end surface of the pushrod is spaced away from the distal end of the elongate member to define a marker recess in the second lumen elongate member for carrying a tissue marker for delivery to a delivery site in a patient.

18 Claims, 19 Drawing Sheets

(52) U.S. Cl.
CPC ...... *A61B 90/39* (2016.02); *A61B 2017/3413* (2013.01); *A61B 2017/3445* (2013.01); *A61B 2090/3908* (2016.02)

(56) References Cited

U.S. PATENT DOCUMENTS

| | | | |
|---|---|---|---|
| 5,795,308 | A | 8/1998 | Russin |
| 5,857,999 | A * | 1/1999 | Quick ............... A61M 25/04 604/174 |
| 6,077,231 | A | 6/2000 | Milliman et al. |
| 6,080,114 | A | 6/2000 | Russin |
| 6,165,136 | A * | 12/2000 | Nishtala ............ A61B 10/0275 604/185 |
| 6,220,248 | B1 | 4/2001 | Voegele et al. |
| 6,228,055 | B1 | 5/2001 | Foerster et al. |
| 6,270,464 | B1 | 8/2001 | Fulton, III et al. |
| 6,471,700 | B1 | 10/2002 | Burbank et al. |
| 6,605,047 | B2 | 8/2003 | Zarins et al. |
| 6,865,470 | B2 | 3/2005 | Burbank et al. |
| 6,875,182 | B2 | 4/2005 | Wardle et al. |
| 6,936,014 | B2 | 8/2005 | Vetter et al. |
| 7,001,341 | B2 | 2/2006 | Gellman et al. |
| 7,083,576 | B2 | 8/2006 | Zarins et al. |
| 7,261,712 | B2 | 8/2007 | Burbank et al. |
| 7,347,829 | B2 | 3/2008 | Mark et al. |
| 7,465,279 | B2 | 12/2008 | Beckman et al. |
| 7,575,556 | B2 | 8/2009 | Speeg et al. |
| 7,862,517 | B2 | 1/2011 | Tsonton et al. |
| 8,075,568 | B2 | 12/2011 | Selis |
| 8,105,243 | B2 | 1/2012 | Vetter |
| 8,167,817 | B2 | 5/2012 | Vetter et al. |
| 8,267,868 | B2 | 9/2012 | Taylor et al. |
| 8,361,082 | B2 | 1/2013 | Jones et al. |
| 8,419,656 | B2 | 4/2013 | Field |
| 8,529,465 | B2 | 9/2013 | Speeg et al. |
| 8,554,309 | B2 | 10/2013 | Hoffa |
| 8,721,563 | B2 | 5/2014 | Taylor et al. |
| 8,728,003 | B2 | 5/2014 | Taylor et al. |
| 8,838,208 | B2 | 9/2014 | Lavelle et al. |
| 8,938,285 | B2 | 1/2015 | Fiebig et al. |
| 9,044,215 | B2 | 6/2015 | Shabaz et al. |
| 9,414,816 | B2 | 8/2016 | Rhad et al. |
| 9,486,162 | B2 | 11/2016 | Zhuang et al. |
| 9,649,093 | B2 | 5/2017 | Burbank et al. |
| 9,993,232 | B2 | 6/2018 | Ellingson et al. |
| 2002/0147413 | A1 * | 10/2002 | Ritchart ............ A61B 10/0266 600/564 |
| 2005/0038355 | A1 | 2/2005 | Gellman et al. |
| 2006/0217635 | A1 | 9/2006 | Mccombs et al. |
| 2006/0224082 | A1 | 10/2006 | Vetter et al. |
| 2007/0299459 | A1 * | 12/2007 | Way ................... A61B 17/34 606/185 |
| 2008/0161720 | A1 | 7/2008 | Nicoson et al. |
| 2010/0063345 | A1 | 3/2010 | Yuasa |
| 2010/0094168 | A1 | 4/2010 | Riek et al. |
| 2010/0261974 | A1 * | 10/2010 | Shelton, IV ....... A61B 17/3439 600/206 |
| 2012/0095434 | A1 * | 4/2012 | Fung ................. A61B 17/3478 604/528 |
| 2012/0165663 | A1 | 6/2012 | Mark et al. |
| 2013/0158388 | A1 | 6/2013 | Blevis |
| 2013/0218047 | A1 * | 8/2013 | Fiebig ............... A61B 10/0283 600/562 |
| 2014/0296647 | A1 * | 10/2014 | Kucklick .......... A61B 17/3421 600/204 |
| 2015/0045665 | A1 | 2/2015 | Lau |
| 2015/0201963 | A1 * | 7/2015 | Snow ................ A61B 10/0233 604/167.03 |
| 2015/0335317 | A1 | 11/2015 | Ellingson et al. |
| 2016/0074131 | A1 | 3/2016 | Lubinski |
| 2016/0256137 | A1 * | 9/2016 | Snow ................ A61B 10/0266 |
| 2017/0143444 | A1 | 5/2017 | Naslund |
| 2020/0359996 | A1 * | 11/2020 | Walsh ................ A61B 90/39 |

FOREIGN PATENT DOCUMENTS

| | | |
|---|---|---|
| WO | 2015187611 A2 | 12/2015 |
| WO | 2015191223 A1 | 12/2015 |
| WO | 2016201115 A1 | 12/2016 |
| WO | 2018145018 A1 | 8/2018 |

* cited by examiner

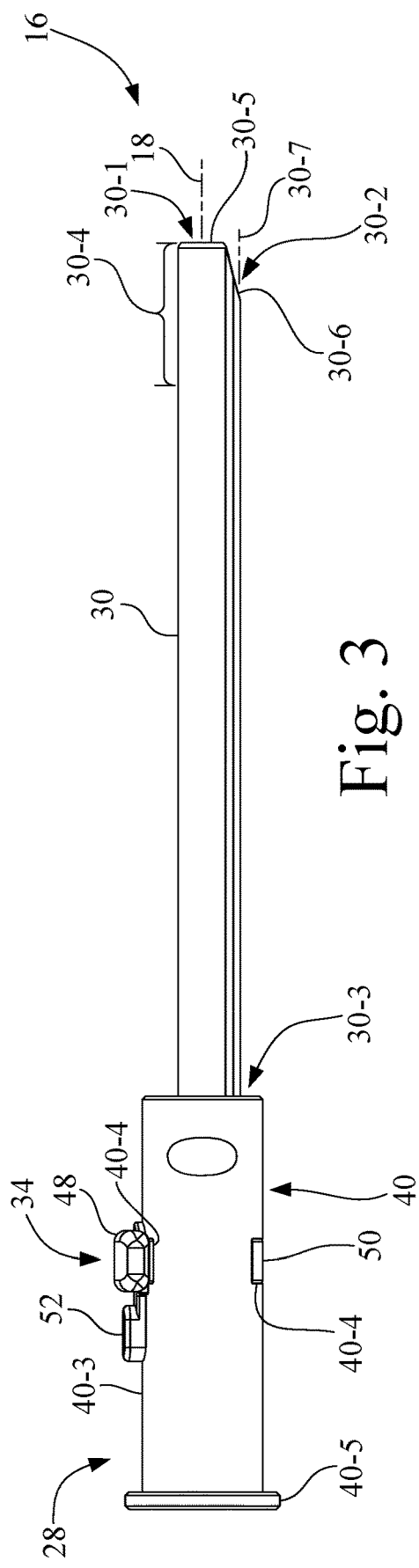
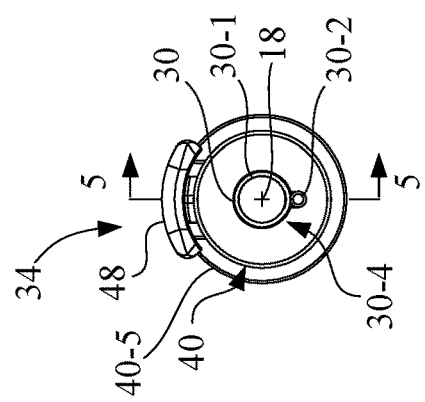
Fig. 3
Fig. 4

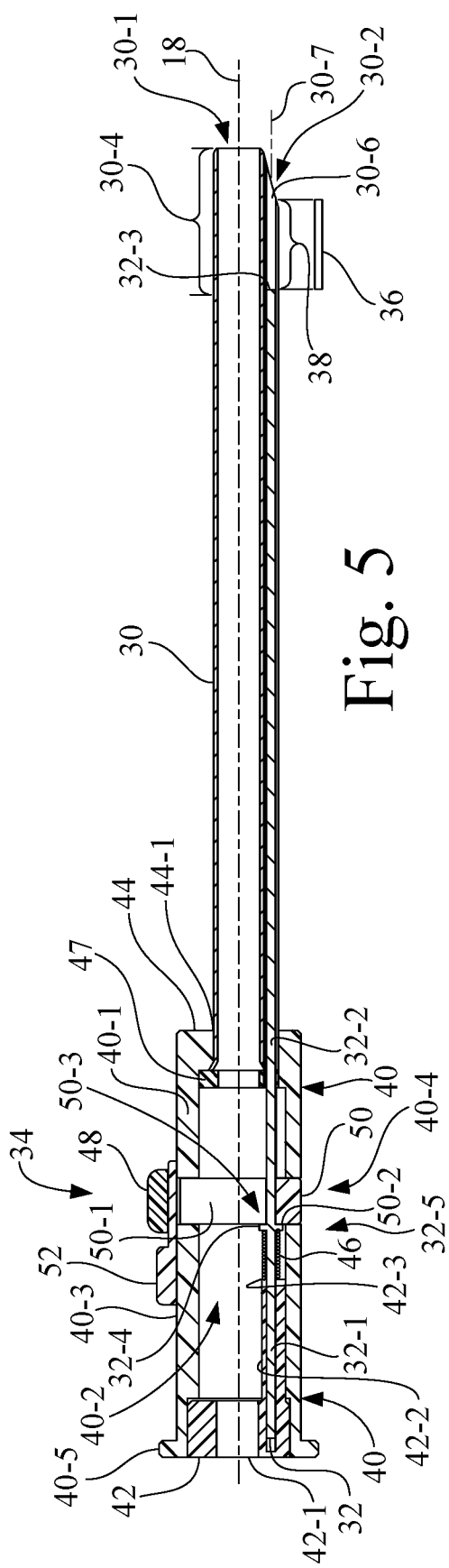
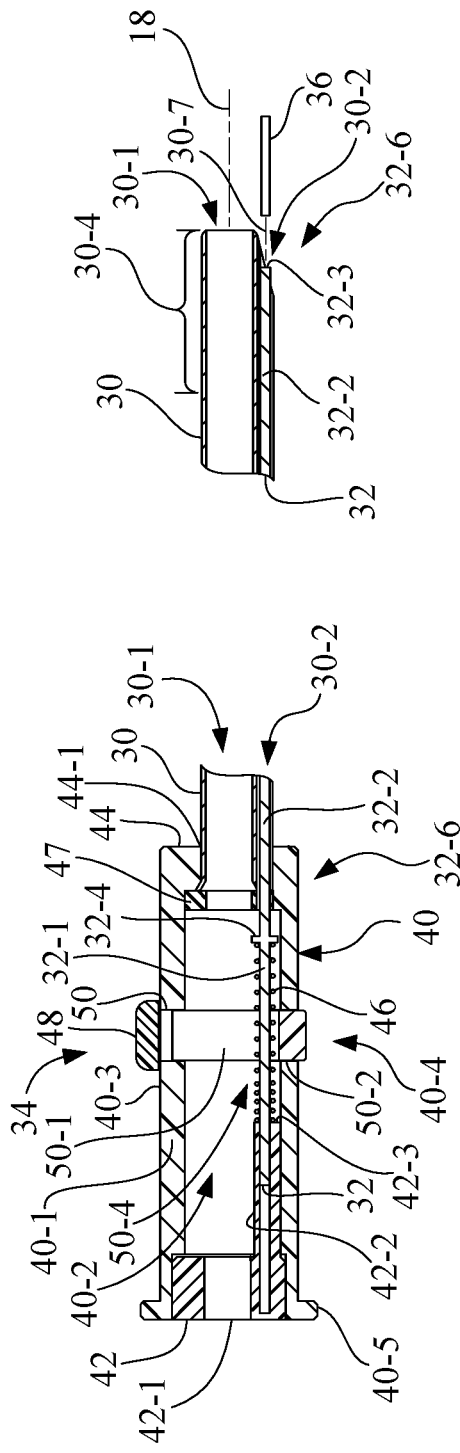
Fig. 5
Fig. 5A
Fig. 5B

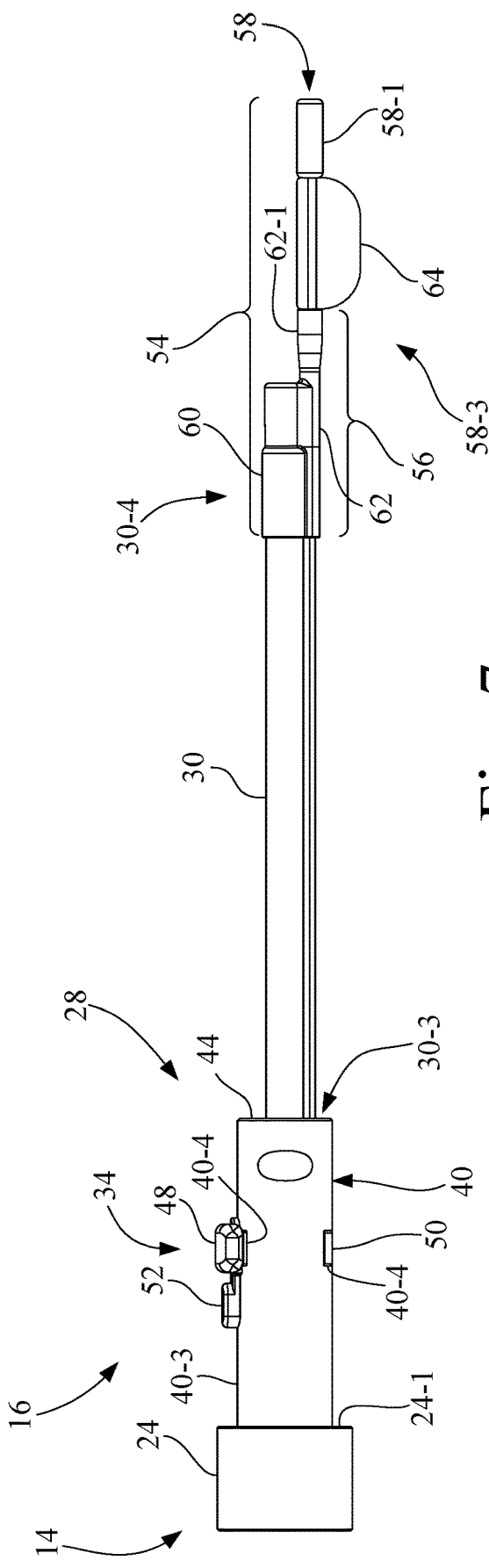
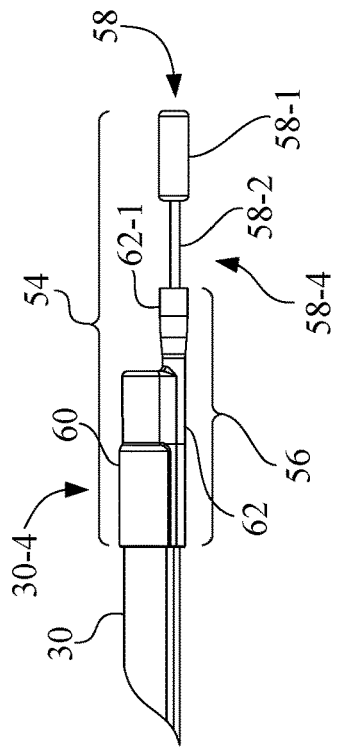
Fig. 7
Fig. 7A

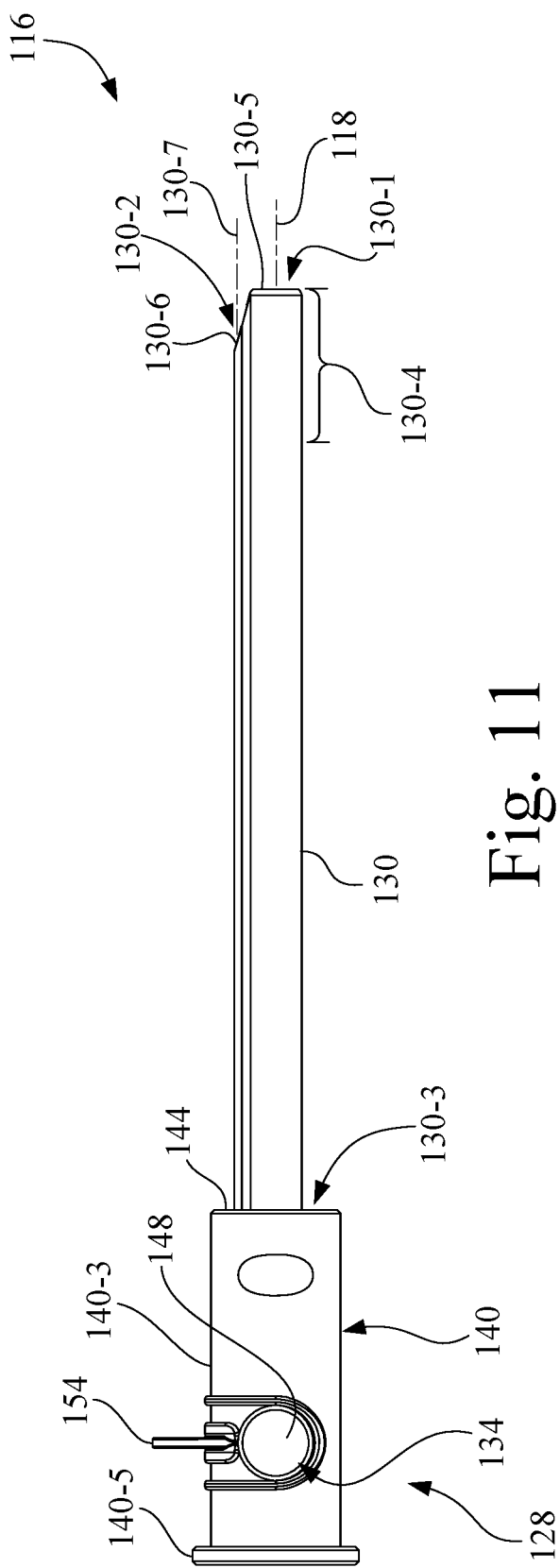
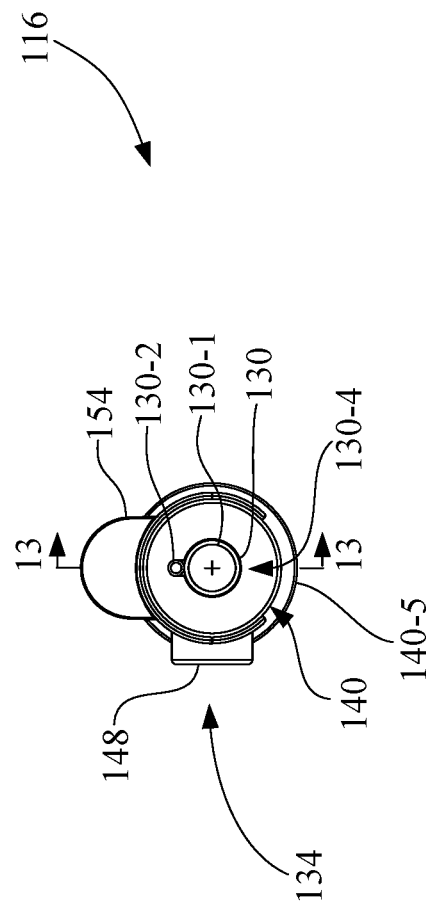
Fig. 11
Fig. 12

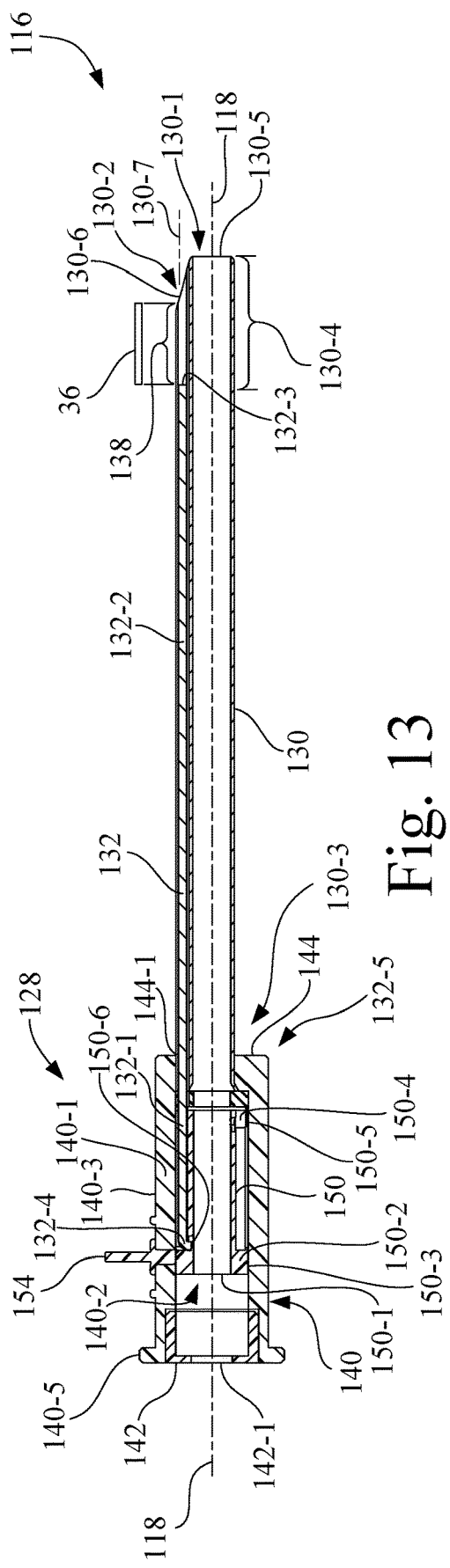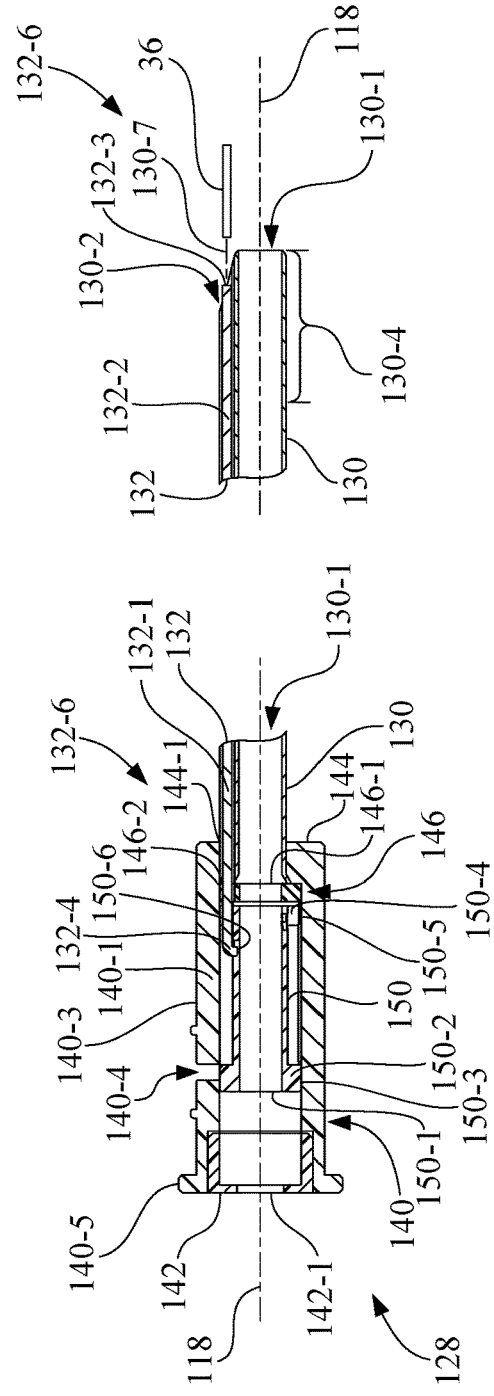
Fig. 13
Fig. 13A
Fig. 13B

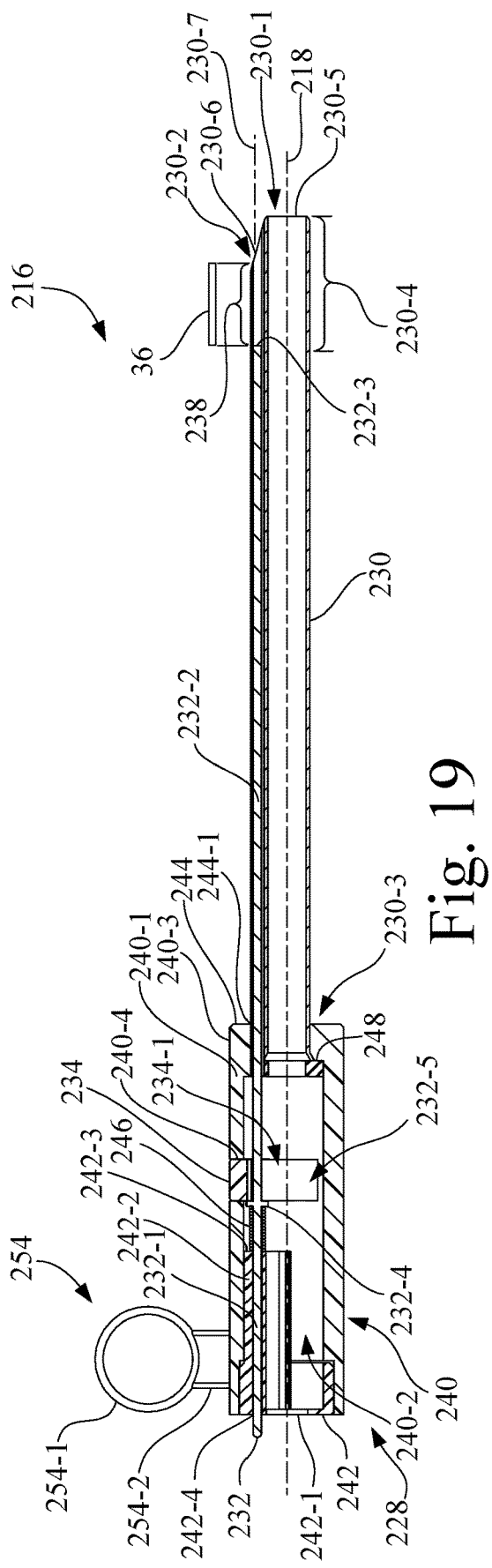
Fig. 19
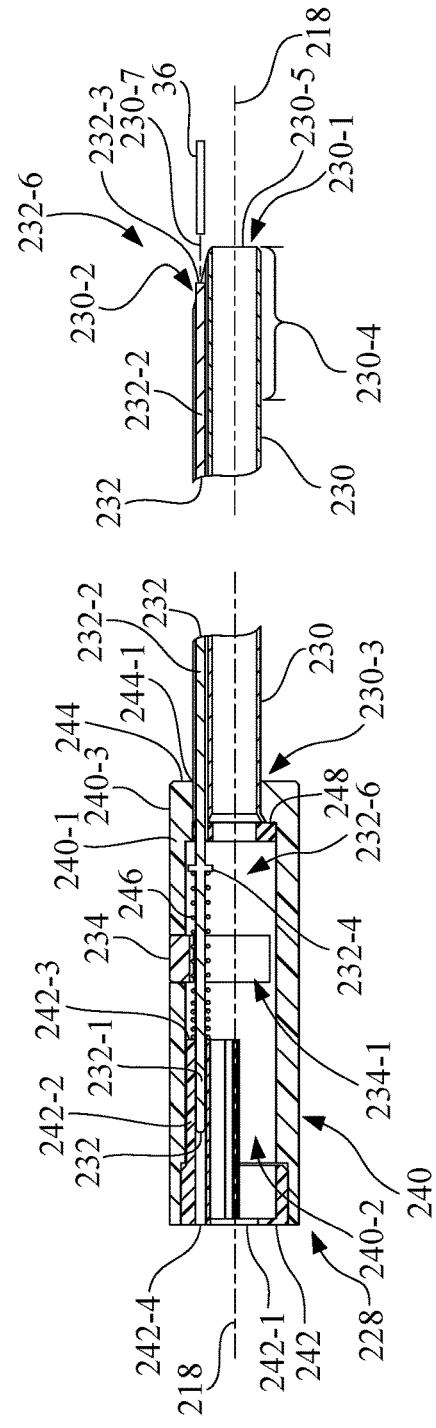
Fig. 19A
Fig. 19B

DUAL LUMEN COAXIAL INTRODUCER HAVING INTEGRATED TISSUE MARKER DELIVERY

CROSS-REFERENCE TO RELATED APPLICATIONS

This application is a U.S. national phase of International Application No. PCT/US2018/028145, filed Apr. 18, 2018, which is incorporated herein by reference in its entirety.

TECHNICAL FIELD

The present invention relates to a biopsy apparatus, and, more particularly, to a dual lumen coaxial introducer having an integrated marker delivery apparatus, for use with an elongate needle of a biopsy device.

BACKGROUND ART

In some image guided medical procedures, such as a biopsy procedure, a tissue marker may be delivered to a biopsy site through a dedicated handheld marker applicator, as is well known in the art.

In one such ultrasound guided procedure, a biopsy needle of a biopsy device is inserted into the patient through a coaxial introducer having a single lumen. In some cases, the coaxial introducer may be pre-positioned at the biopsy site through the use of a trocar that protrudes distally from the lumen of the coaxial introducer and is inserted into the patient, wherein the trocar is then removed and replaced with the biopsy needle. The biopsy device is then operated to take a tissue sample. Thereafter, the biopsy needle is removed from the coaxial introducer, and the marker applicator is inserted through the lumen of the coaxial introducer. The marker applicator is then operated to deliver the marker to the biopsy site. This ultrasound guided biopsy/marker placement procedure may be perceived by some users as being cumbersome, because the user must be able to manipulate the ultrasound probe using one hand, while switching out the biopsy device and the handheld marker applicator with the other hand.

In another such ultrasound guided procedure, a biopsy needle of a biopsy device is introduced into the patient. The biopsy device is then operated to take a tissue sample. Thereafter, a pathway is opened to the lumen of the biopsy needle, and the marker applicator is inserted into the pathway and through the lumen of biopsy needle. The marker applicator is then operated to deliver the marker to the biopsy site. This procedure may be perceived by some users as being cumbersome, because the user must be able to manipulate the ultrasound probe with one hand and hold the biopsy device with the other hand, with no free hand being available to manipulate the handheld marker applicator.

What is needed in the art is an apparatus that simplifies typical biopsy and tissue marker placement procedures.

SUMMARY OF INVENTION

The present invention provides a dual lumen coaxial introducer having integrated marker delivery, for use with an elongate needle, such as the elongate needle of a biopsy device.

The invention, in one form, is directed to a dual lumen coaxial introducer, for use with an elongate needle, which includes a hub, an elongate member, and a pushrod. The elongate member has a first lumen, a second lumen, a proximal end portion, and a distal end. The proximal end portion is fixedly attached to the hub. The first lumen of the elongate member defines a longitudinal axis and is configured to slidably receive the elongate needle. The pushrod is located in the second lumen of the elongate member. The pushrod has a distal end surface. The pushrod is movable in the second lumen between a retracted position and an extended position. In the retracted position, the distal end surface of the pushrod is spaced away from the distal end of the elongate member to define a marker recess in the second lumen elongate member for carrying a tissue marker for delivery to a delivery site.

The invention, in another form, is directed to a biopsy system that includes a biopsy device and a dual lumen coaxial introducer. The biopsy device has a device body and an elongate needle that extends distally from the device body. The elongate needle has a cutting distal end. The dual lumen coaxial introducer includes a hub, an elongate member, and a pushrod. The hub is configured for releasable attachment to the biopsy device. The elongate member has a first lumen, a second lumen, a proximal end portion, and a distal end. The proximal end portion is fixedly attached to the hub. The first lumen defines a longitudinal axis and is configured to slidably receive the elongate needle of the biopsy device. The pushrod is located in the second lumen. The pushrod has a distal end surface. The pushrod is movable between a retracted position and an extended position. In the retracted position, the distal end surface of the pushrod is spaced away from the distal end of the elongate member to define a marker recess in the second lumen for carrying a tissue marker for delivery to a delivery site.

An advantage of the present invention is that the dual lumen coaxial introducer of the present invention has a dedicated needle lumen to receive and guide the elongate member, e.g., needle, of the biopsy device and has a dedicated marker lumen to carry and deliver a pre-loaded tissue marker, and with the dual lumen coaxial introducer having mechanical features to eject the tissue marker at a site within a patient, such as at a biopsy site, without necessitating removal, or a change in the configuration, of the installed biopsy device, e.g., the sample-taking biopsy device or the trocar biopsy device.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 3 is a side view of the dual lumen coaxial introducer of FIGS. 1 and 2;

FIG. 4 is an end view of the dual lumen coaxial introducer of FIG. 3;

FIG. 5 is a section view of the dual lumen coaxial introducer of FIG. 3, taken along line 5-5 of FIG. 4, showing a pushrod in the tissue marker lumen in a retracted position, a spring in a compressed state, and with an engagement member of the actuator in an engaged position to engage the flange of the pushrod;

FIG. 5A is a portion of the section view of FIG. 5, with the pushrod in the extended position;

FIG. 5B is a portion of the section view of FIG. 5, with the engagement member of the actuator in a release position wherein the spring has decompressed to move the pushrod from the retracted position depicted in FIG. 5 to the extended position depicted in FIG. 5A;

FIG. 7 is a side view of the configuration of the dual lumen coaxial introducer and the trocar of FIG. 2, with a marker loader installed on a distal end portion of the dual lumen coaxial introducer and having a marker delivery plunger in a holding position;

FIG. 7A is a portion of the side view of FIG. 7, with the marker delivery plunger in a loaded position, having delivered the tissue marker into the marker recess in the second lumen of the elongate member of the dual lumen coaxial introducer;

FIG. 11 is a side view of the dual lumen coaxial introducer of FIGS. 9 and 10;

FIG. 12 is an end view of the dual lumen coaxial introducer of FIG. 10;

FIG. 13 is a section view of the dual lumen coaxial introducer of FIG. 11, taken along line 13-13 of FIG. 12, showing a pushrod in the tissue marker lumen in a retracted position;

FIG. 13A is a portion of the section view of FIG. 13, with the pushrod in the extended position;

FIG. 13B is a portion of the section view of FIG. 13, with the cylindrical body of the actuator in a position having moved the pushrod from the retracted position depicted in FIG. 13 to the extended position depicted in FIG. 13A;

FIG. 19 is a section view of the dual lumen coaxial introducer of FIG. 16, taken along line 19-19 of FIG. 18, showing a pushrod in the tissue marker lumen in a retracted position, a spring in a compressed state, and a flange of the pushrod engaged with an engagement member;

FIG. 19A is a portion of the section view of FIG. 19, with the pushrod in the extended position;

FIG. 19B is a portion of the section view of FIG. 19, showing the spring decompressed to move the pushrod from the retracted position depicted in FIG. 19 to the extended position depicted in FIG. 19A.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
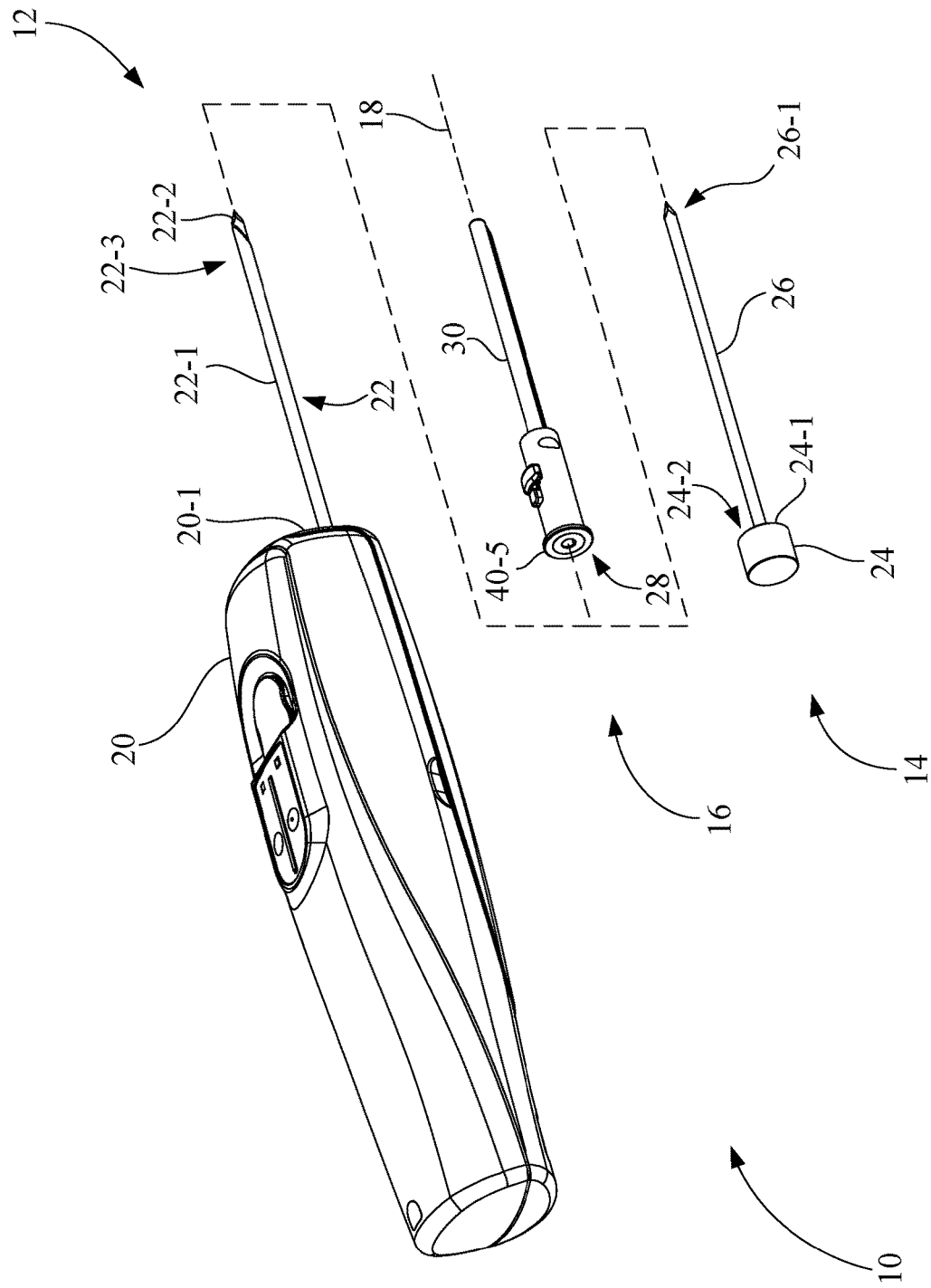
FIG. 1 is a perspective view of a biopsy system having a sample-taking biopsy device, a trocar biopsy device, and a dual lumen coaxial introducer, in accordance with an embodiment of the present invention.

Referring now to the drawings, and more particularly to FIG. 1, there is shown a biopsy system 10 of an embodiment of the present invention.

Biopsy system 10 includes a biopsy device 12; a biopsy device 14, hereinafter referred to as trocar 14; and a dual lumen coaxial introducer 16 configured in accordance with an aspect of the present invention. As depicted, dual lumen coaxial introducer 16 is configured to receive either of biopsy device 12 or trocar 14 along a longitudinal axis 18 of dual lumen coaxial introducer 16. In addition, in accordance with an aspect of the present invention, dual lumen coaxial introducer 16 is configured with a dedicated marker lumen to carry a pre-loaded tissue marker 36 (see FIG. 5), and to eject tissue marker 36 at a site within a patient, such as a biopsy site, without necessitating removal or change in configuration of the installed biopsy device, e.g., biopsy device 12 or trocar 14.

Biopsy device 12, such as the Finesse™ brand biopsy device available from C.R. Bard, Inc., has a device body 20 and an elongate needle 22 that extends distally from device body 20. Elongate needle 22 may form a portion of a releasable biopsy probe, as is known in the art, and in the context of the present application, a housing of such releasable biopsy probe is considered to be part of device body 20. Elongate needle 22 may include a cutting cannula 22-1 and a stylet 22-2. Elongate needle 22 has a cutting distal end 22-3 to effect tissue piercing and cutting in performing a biopsy procedure, in a manner known in the art. Device body 20 contains driving components that couple to elongate needle 22 for performing a biopsy procedure in a manner as is known in the art. Device body 20 includes a mounting portion 20-1 for releasable attachment to dual lumen coaxial introducer 16. In the present embodiment, mounting portion 20-1 may be configured as a friction-fit cylinder for receiving a proximal end, e.g., proximal mounting flange 40-5, of dual lumen coaxial introducer 16.

Figure 2:
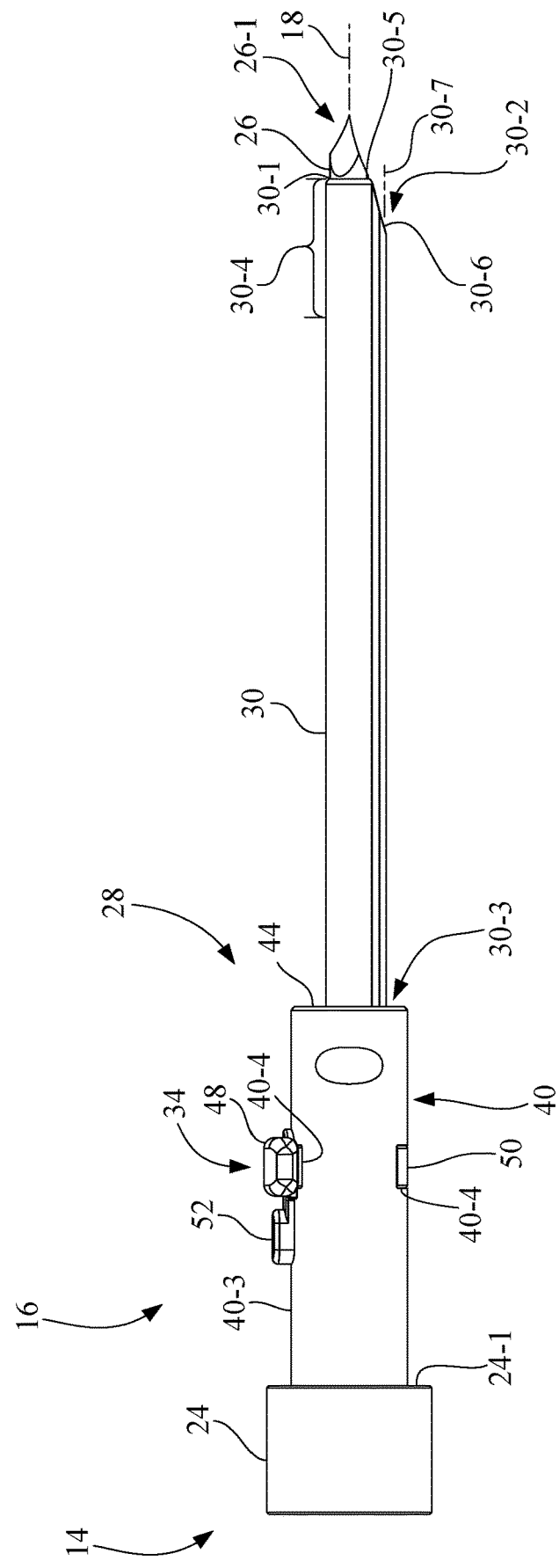
FIG. 2 is a side view of a configuration of components of FIG. 1, having the dual lumen coaxial introducer installed on the trocar.

Referring to FIGS. 1 and 2, trocar 14 includes a trocar body 24 and an elongate needle 26 that extends distally from trocar body 24. Trocar body 24 includes a mounting portion 24-1 for releasable attachment to dual lumen coaxial introducer 16. Mounting portion 24-1 may be configured, for example, as a friction-fit cylinder 24-2 for receiving a proximal end, e.g., proximal mounting flange 40-5, of dual lumen coaxial introducer 16. Elongate needle 26 has a cutting distal end 26-1, e.g., a pointed tip portion, for piercing tissue.

In preparation for a biopsy procedure, for example, dual lumen coaxial introducer 16 may be installed on trocar 14, as shown in FIG. 2. During the biopsy procedure, under image guidance, such as by ultrasound, the trocar/introducer combination 14/16 may then be inserted into the patient, with dual lumen coaxial introducer 16 proximal to the biopsy site in the patient. Trocar 14 is then decoupled from dual lumen coaxial introducer 16, and trocar 14 is removed from dual lumen coaxial introducer 16, with dual lumen coaxial introducer 16 maintaining the pathway to the biopsy site originally opened using trocar 14. Then, elongate needle 22 of biopsy device 12 is guided to the biopsy site by dual lumen coaxial introducer 16 to remove a tissue sample. Alternatively, in some procedures, elongate needle 22 of biopsy device 12 may perform the functions of trocar 14. Without necessitating removal or change in configuration of the installed biopsy device, e.g., biopsy device 12, dual lumen coaxial introducer 16 may be operated to deliver a tissue marker that was pre-loaded into a dedicated marker lumen of dual lumen coaxial introducer 16.

Referring also to FIGS. 3-6, dual lumen coaxial introducer 16 includes a hub 28, an elongate member 30, a pushrod 32, and an actuator 34. As shown in FIG. 5, dual lumen coaxial introducer 16 is configured to carry tissue marker 36.

Hub 28, having proximal mounting flange 40-5, is configured for releasable attachment to either of device body 20 of biopsy device 12 or trocar body 24 of trocar 14.

In the present embodiment, elongate member 30 has a first lumen 30-1, a second lumen 30-2, a proximal end portion 30-3, a distal end portion 30-4, a blunt distal end 30-5, and a beveled distal end 30-6. First lumen 30-1 defines longitudinal axis 18, and distally terminates at blunt distal end 30-5. Second lumen 30-2 defines a pushrod axis 30-7, and distally terminates at beveled distal end 30-6.

Proximal end portion 30-3 of elongate member 30 is fixedly attached to hub 28, e.g., by over-mold, press fit, adhesive, weld, etc. First lumen 30-1 is sized and shaped to slidably receive either of elongate needle 22 of biopsy device 12 or elongate needle 26 of trocar 14. Second lumen 30-2 is sized and shaped to slidably receive pushrod 32 for movement along pushrod axis 30-7 and to carry tissue marker 36 for future deployment. Elongate member 30 may be formed from two joined cannula, as shown for example in FIGS. 2-6, respectively having first lumen 30-1 and second lumen 30-2. Alternatively, elongate member 30 may be formed as a single elongate member having two bores respectively corresponding to first lumen 30-1 and second lumen 30-2.

Pushrod 32 is located in second lumen 30-2 of elongate member 30 for sliding movement along pushrod axis 30-7. Pushrod 32 may be formed as a unitary member that has a proximal portion 32-1, a distal portion 32-2, a distal end surface 32-3, and a flange 32-4. Flange 32-4 is interposed between proximal portion 32-1 and distal portion 32-2. Pushrod 32 is movable between a retracted position 32-5 shown in FIG. 5 and an extended position 32-6 shown in FIGS. 5A and 5B.

Referring to FIG. 5, in retracted position 32-5, distal end surface 32-3 of pushrod 32 is spaced away from beveled distal end 30-6 of elongate member 30 to define a marker recess 38 in second lumen 30-2 of elongate member 30 that will receive and carry tissue marker 36. With tissue marker 36 positioned in marker recess 38 of second lumen 30-2, when pushrod 32 is moved from retracted position 32-5 (FIG. 5) to extended position 32-6 (FIGS. 5A and 5B), tissue marker 36 is expelled from second lumen 30-2 and deposited at the biopsy site.

Hub 28 includes a hub body 40, a proximal end wall 42, and a distal end wall 44. Hub body 40 has a side wall 40-1 that defines a hollow interior 40-2 and an exterior surface 40-3. Hub body 40 has a guide channel 40-4 that extends through side wall 40-1 from exterior surface 40-3 to hollow interior 40-2, and in turn, guide channel extends through an entirety of hub body 40. Hub body 40 may further include proximal mounting flange 40-5, which is sized and shaped for releasable engagement with either of mounting portion 20-1 of biopsy device 12 or mounting portion 24-1 of trocar body 24 of trocar 14. Proximal end wall 42 and distal end wall 44 are spaced apart along the longitudinal axis 18.

Proximal end wall 42 of hub 28 may be configured as an insert, e.g., a plastic insert, to be inserted into a proximal opening in hub body 40, and fixedly attached to hub body 40, such as by adhesive, weld, etc. Proximal end wall 42 of hub 28 has a hole 42-1 centered on longitudinal axis 18 sized and shaped to slidably receive either of elongate needle 22 of biopsy device 12 or elongate needle 26 of trocar 14. Proximal end wall 42 also includes a distally extending arm 42-2 that defines a spring seat 42-3.

Distal end wall 44 of hub 28 may be configured as an end wall extension of hub body 40. Distal end wall 44 has a hole 44-1 sized and shaped to receive and mount proximal end portion 30-3 of elongate member 30, e.g., by over-mold, press fit, adhesive, weld, etc.

A spring 46, e.g., a coil spring, is positioned over proximal portion 32-1 of pushrod 32, and is positioned between the spring seat 42-3 of proximal end wall 42 of hub 28 and flange 32-4 of pushrod 32. When pushrod 32 is in retracted position 32-5 (see FIG. 5), spring 46 is in a compressed state and when pushrod 32 is in extended position 32-6 (see FIG. 5B), spring 46 is relaxed from the compressed state, i.e., is decompressed to an extended condition.

A seal member 47 is positioned adjacent to, and in sealing engagement with, distal end wall 44 in hollow interior 40-2 so as to form a seal with distal end wall 44 around hole 44-1. Seal member 47 has a hole 47-1 and a hole 47-2. Hole 47-1 of seal member 47 and hole 42-1 of proximal end wall 42 are aligned along longitudinal axis 18. Hole 47-1 of seal member 47 is sized and shaped to slidably receive either of elongate needle 22 of biopsy device 12 or elongate needle 26 of trocar 14 in sealing engagement.

In seal member 47, hole 47-2 is centered on pushrod axis 30-7 and is radially spaced, relative to longitudinal axis 18, from the hole 47-1. Hole 47-2 is sized and shaped to slidably accommodate pushrod 32 in sealing engagement. When dual lumen coaxial introducer 16 is fully assembled, distal portion 32-2 of pushrod 32 is slidably received and slidably resides in hole 47-2 of seal member 47 and in second lumen 30-2 of elongate member 30.

In the present embodiment, seal member 47 may be made in its entirety of an elastomer, e.g., rubber, to form a seal at hole 47-1 to engage the circumferential surface of the elongate needle, e.g., elongate needle 22 of biopsy device 12 or elongate needle 26 of trocar 14, and to form a seal at hole 47-2 to engage the circumferential surface of the distal portion 32-2 of pushrod 32. Alternatively, sealing at distal end wall 44 may be provided by discrete seal members, such as respective O-rings located in distal end wall 44 to form hole 47-1 and to form hole 47-2. Such sealing prevents fluids at the biopsy site from passing proximally into hub body 40.

Referring to FIGS. 5 and 5B, actuator 34 is mounted to hub 28. Actuator 34 is configured to be operable by a user to facilitate movement of pushrod 32 from retracted position 32-5 (see FIG. 5) to extended position 32-6 (see FIGS. 5A and 5B) to expel tissue marker 36 from second lumen 30-2. Actuator 34 is configured as a button assembly having actuator button 48 attached to an engagement member 50.

Figure 6:
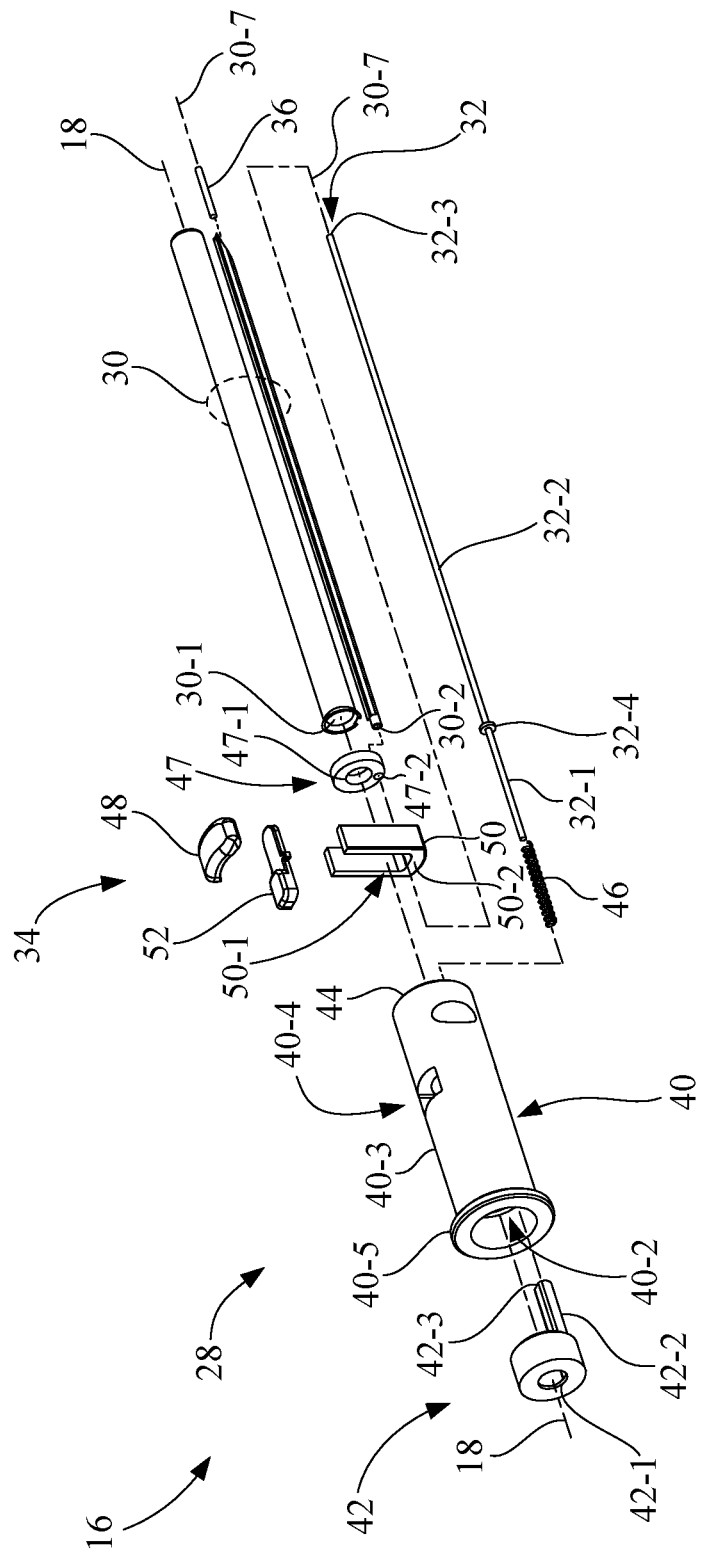
FIG. 6 is an exploded view of the dual lumen coaxial introducer of FIGS. 3 and 4.

Referring also to FIG. 6, actuator button 48 projects outwardly from guide channel 40-4 of hub body 40.

Engagement member 50 is positioned in guide channel 40-4 of hub body 40 to extend into and through the hollow interior 40-2 of hub body 40. In the present embodiment, engagement member 50 may be formed, for example, as a U-shaped structure that is fixedly attached to actuator button 48. Engagement member 50 has a passage 50-1 defined by the U-shaped structure, in which pushrod 32 movably resides. Engagement member 50 also defines a proximal engagement surface 50-2 for engagement with flange 32-4 of pushrod 32.

Actuator button 48 is configured to move engagement member 50 in guide channel 40-4 from an engaged position 50-3 (see FIG. 5) to a release position 50-4 (see FIG. 5B) to facilitate movement of pushrod 32 from retracted position 32-5 depicted in FIG. 5 to extended position 32-6 depicted in FIG. 5A.

Referring to FIG. 5, when pushrod 32 is in retracted position 32-5 and engagement member 50 of actuator 34 is in engaged position 50-3, flange 32-4 of pushrod 32 is engaged with proximal engagement surface 50-2 of engagement member 50 with spring 46 being held in the compressed state. When a user applies an external force to actuator button 48 of actuator 34 to move actuator button 48 in a direction toward pushrod 32, i.e., the user depresses actuator button 48, engagement member 50 is moved downwardly, i.e., depressed, to release position 50-4 (see FIG. 5B), whereby proximal engagement surface 50-2 of engagement member 50 is moved out of engagement with flange 32-4 of pushrod 32 to release spring 46 from the compressed state. As spring 46 decompresses, pushrod 32 is moved by the spring force exerted by spring 46 against flange 32-4 from retracted position 32-5 to extended position 32-6 (see FIGS. 5A and 5B).

Referring to FIGS. 2-5 and 6, a safety insert 52 may be interposed, in a sliding action, between actuator 34 and hub 28 to prevent operation of actuator 34 to until safety insert 52 is removed. More particularly, safety insert 52 is inserted between actuator button 48 of actuator 34 and exterior surface 40-3 of hub body 40 of hub 28.

Figure 8:
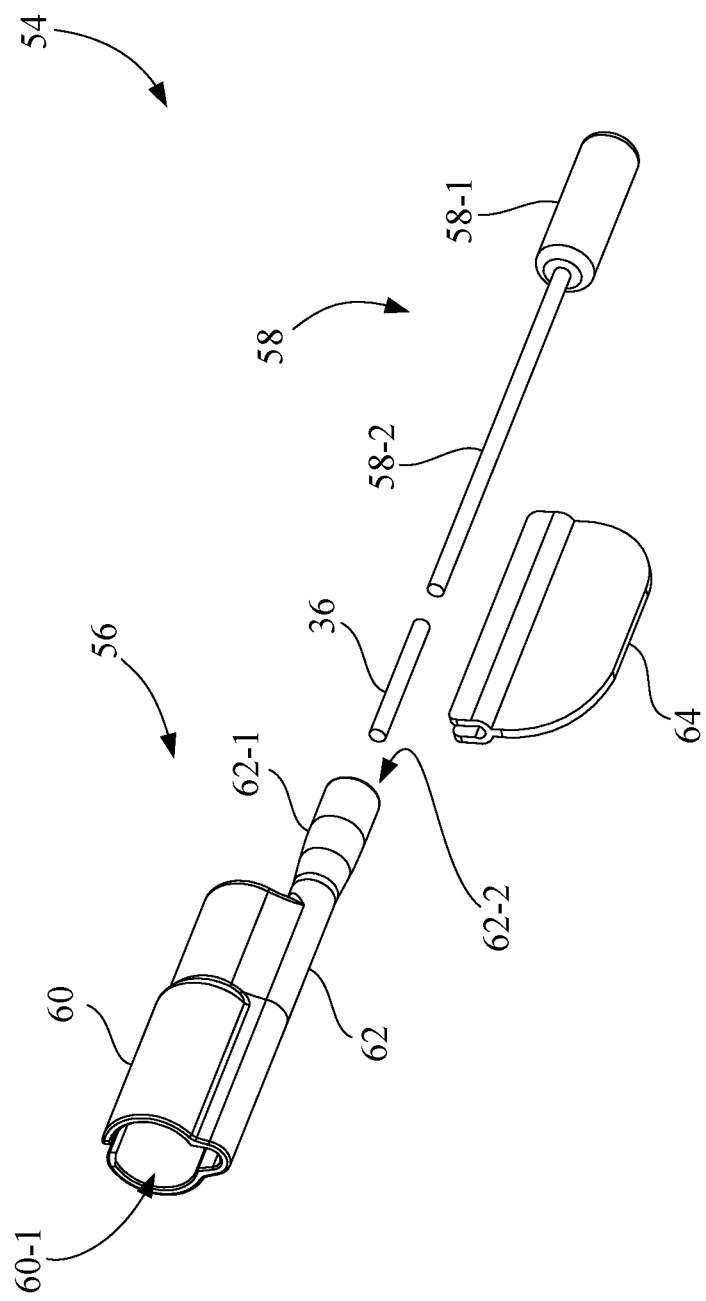
FIG. 8 is an exploded view of the marker loader of FIG. 7.

Referring to FIGS. 7-8 in conjunction with FIGS. 2 and 5, biopsy system 10 may further include a marker loader 54 configured to load tissue marker 36 into marker recess 38 in second lumen 30-2 of elongate member 30. Marker loader 54 includes a loader body 56 and a plunger 58.

Loader body 56 has a mounting portion 60 and a marker tube 62. Marker tube 62 is sized and shaped to carry the tissue marker 36 that is to be transferred (loaded) into marker recess 38 in second lumen 30-2 of elongate member 30. The tissue marker input end portion 62-1 of marker tube 62 is flared, i.e., bell-shaped, to aid in the insertion of tissue marker 36 into marker tube 62 of marker loader 54.

Mounting portion 60 has a receptacle recess 60-1 (see FIG. 8). Receptacle recess 60-1 of mounting portion 60 is configured to be received over distal end portion 30-4 of elongate member 30 to align a lumen 62-2 of marker tube 62 of loader body 56 with second lumen 30-2 of elongate member 30 (see FIGS. 5, 7 and 7A). In the present embodiment, distal end portion 30-4 of elongate member 30 has an external figure-8 transverse shape (see FIG. 4), and receptacle recess 60-1 of mounting portion 60 of loader body 56 has a corresponding internal figure-8 transverse shape (see FIG. 8) to slidably receive distal end portion 30-4 of elongate member 30 in a snug fit.

Referring to FIG. 8, plunger 58 has a head portion 58-1 and a shaft portion 58-2. Shaft portion 58-2 is slidably received in marker tube 62. Plunger 58 is sized and shaped to move in marker tube 62 between a holding position 58-3 (see FIG. 7) and a transferred position 58-4 (see FIG. 7A). In holding position 58-3, tissue marker 36 is contained in marker tube 62. In transferred position 58-4 (see FIG. 7A), tissue marker 36 is transferred from marker tube 62 of loader body 56 into marker recess 38 in second lumen 30-2 of elongate member 30.

Referring to FIGS. 7 and 8, optionally, a safety insert 64 may be interposed between head portion 58-1 of plunger 58 and loader body 56 to prevent operation of plunger 58 of marker loader 54 to until safety insert 64 is removed. In the present embodiment, safety insert 64 is in the form of a clip that clips over shaft portion 58-2 of plunger 58 of marker loader 54. Referring to FIG. 7A in relation to FIG. 5, once safety insert 64 is removed, plunger 58 of marker loader 54 may be slid in marker tube 62 in a direction toward marker recess 38 in second lumen 30-2 of elongate member 30 so as to load tissue marker 36 into marker recess 38 in second lumen 30-2 of elongate member 30.

Figure 9:
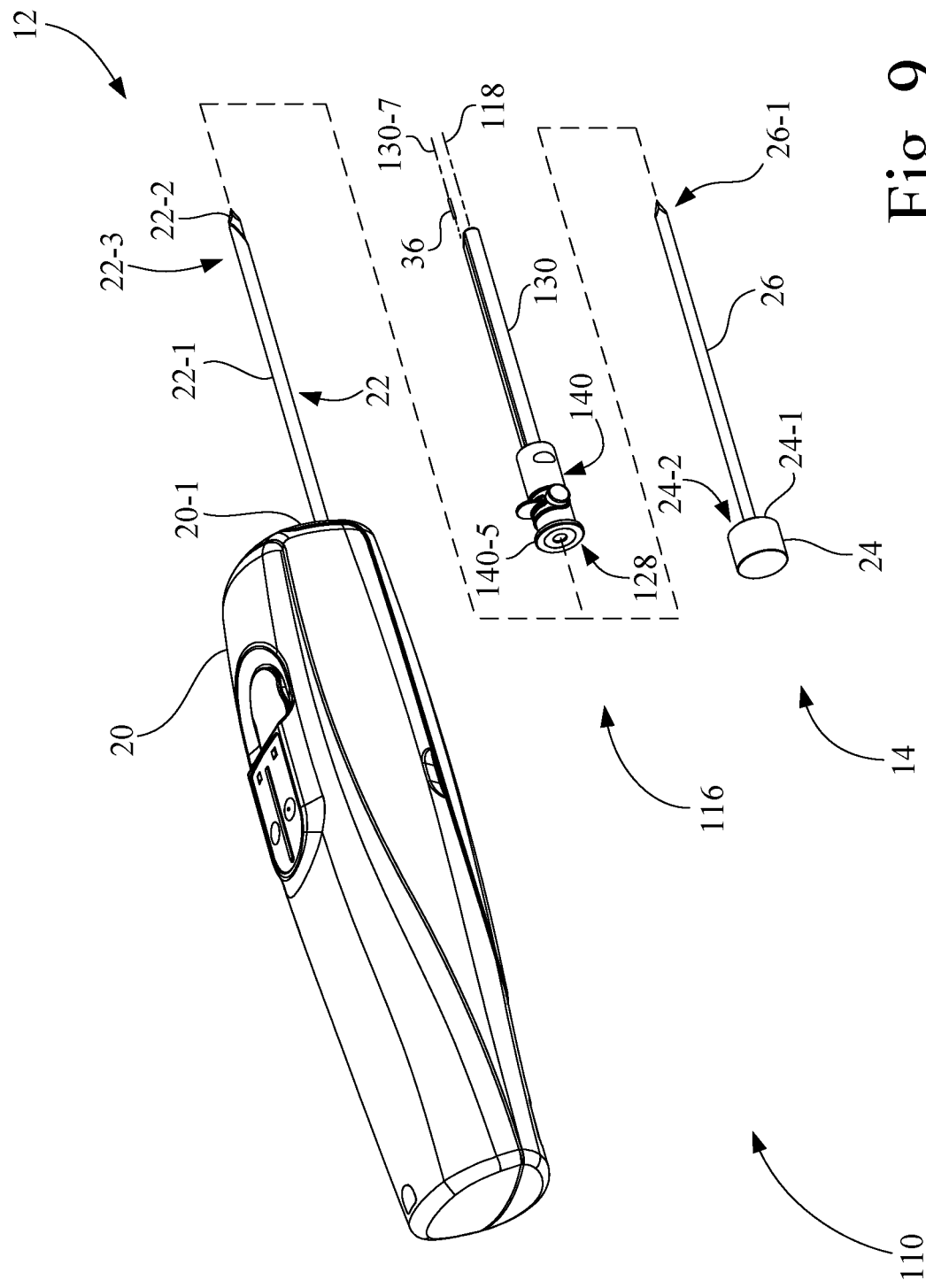
FIG. 9 is a perspective view of another biopsy system having a sample-taking biopsy device, a trocar biopsy device, and a dual lumen coaxial introducer, in accordance with another embodiment of the present invention.

FIG. 9 shows a biopsy system 110 having a dual lumen coaxial introducer in accordance with another embodiment of the present invention. FIG. 9, in relation to FIG. 1, shows a dual lumen coaxial introducer 116 that may be substituted for dual lumen coaxial introducer 16 described above with respect to FIGS. 1-8. More particularly, biopsy system 110 includes biopsy device 12; biopsy device 14, hereinafter referred to as trocar 14; and dual lumen coaxial introducer 116. Biopsy device 12 and biopsy device (trocar) 14 of FIG. 9 are identical to that of FIG. 1 and described above.

As depicted in FIG. 9, dual lumen coaxial introducer 116 is configured to receive either of biopsy device 12 or trocar 14 along a longitudinal axis 118 of dual lumen coaxial introducer 116. In addition, in accordance with an aspect of the present invention, dual lumen coaxial introducer 116 is configured with a dedicated marker lumen to carry the pre-loaded tissue marker 36, and to eject tissue marker 36 at a site within a patient, such as a biopsy site, without necessitating removal or change in configuration of the installed biopsy device, e.g., biopsy device 12 or trocar 14.

Device body 20 of biopsy device 12 includes a mounting portion 20-1, e.g., a friction-fit cylinder, for releasable attachment to a proximal mounting flange 140-5, of dual lumen coaxial introducer 116. Likewise, mounting portion 24-1 of trocar body 24 of trocar 14 includes mounting portion 24-1, e.g., as a friction-fit cylinder 24-2, for releasable attachment to proximal mounting flange 140-5 of dual lumen coaxial introducer 116.

Referring also to FIGS. 10-14, dual lumen coaxial introducer 116 includes a hub 128, an elongate member 130, a pushrod 132, and an actuator 134. As shown in FIG. 13, dual lumen coaxial introducer 116 is configured to carry tissue marker 36.

Hub 128, having proximal mounting flange 140-5, is configured for releasable attachment to either of device body 20 of biopsy device 12 or trocar body 24 of trocar 14.

In the present embodiment, elongate member 130 has a first lumen 130-1, a second lumen 130-2, a proximal end portion 130-3, a distal end portion 130-4, a blunt distal end 130-5, and a beveled distal end 130-6. First lumen 130-1 defines longitudinal axis 118, and distally terminates at blunt distal end 130-5. Second lumen 130-2 defines a pushrod axis 130-7, and distally terminates at beveled distal end 130-6.

Proximal end portion 130-3 of elongate member 130 is fixedly attached to hub 128, e.g., by over-mold, press fit, adhesive, weld, etc. First lumen 130-1 is sized and shaped to slidably receive either of elongate needle 22 of biopsy device 12 or elongate needle 26 of trocar 14. Second lumen 130-2 is sized and shaped to slidably receive pushrod 132 for movement along pushrod axis 130-7 and to carry tissue marker 36 for future deployment. Elongate member 130 may be formed from two joined cannula, as shown for example in FIGS. 10-15, respectively having first lumen 130-1 and second lumen 130-2. Alternatively, elongate member 130 may be formed as a single elongate member having two bores respectively corresponding to first lumen 130-1 and second lumen 130-2.

Figure 14:
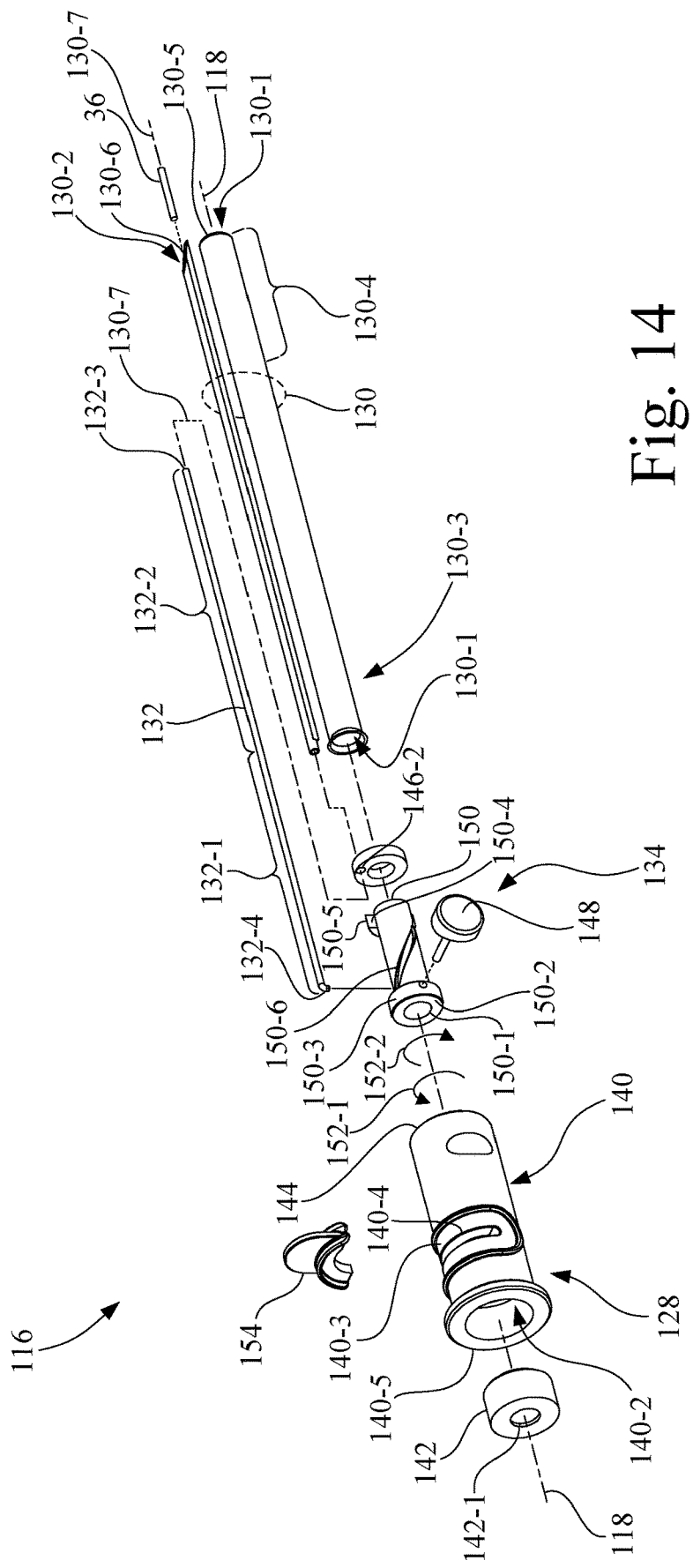
FIG. 14 is an exploded view of the dual lumen coaxial introducer of FIGS. 11 and 12.

Referring to FIGS. 13-14, pushrod 132 is located in second lumen 130-2 of elongate member 130 for sliding movement along pushrod axis 130-7. Pushrod 132 may be formed as a unitary member that has a proximal portion 132-1, a distal portion 132-2, and a distal end surface 132-3. The proximal portion 132-1 has a drive protrusion 132-4, which may be in the form of an elbow bend at approximately 90 degrees (range of 90 degrees+10 degrees) with respect to pushrod axis 130-7. Distal portion 132-2 is slidably received in second lumen 130-2 of elongate member 130. Pushrod 132 is movable between a retracted position 132-5 shown in FIG. 13 and an extended position 132-6 shown in FIGS. 13A and 13B.

Referring to FIG. 13, in retracted position 132-5, distal end surface 132-3 of pushrod 132 is spaced away from beveled distal end 130-6 of elongate member 130 to define a marker recess 138 in second lumen 130-2 of elongate member 130 that will receive and carry tissue marker 36. With tissue marker 36 positioned in marker recess 138 of second lumen 130-2, when pushrod 132 is moved from retracted position 132-5 (FIG. 13) to extended position 132-6 (FIGS. 13A and 13B), tissue marker 36 is expelled from second lumen 130-2 and deposited at the biopsy site.

Hub 128 includes a hub body 140, a proximal end wall 142, and a distal end wall 144. Hub body 140 has a side wall 140-1 that defines a hollow interior 140-2 and an exterior surface 140-3. Proximal end wall 142 and distal end wall 144 are spaced apart along the longitudinal axis 118. Hub body 140 may include proximal mounting flange 140-5, which is sized and shaped for releasable engagement with either of mounting portion 20-1 of biopsy device 12 or mounting portion 24-1 of trocar body 24 of trocar 14.

Hub body 140 has a guide slot 140-4 (see FIG. 13B) that extends through side wall 140-1 from exterior surface 140-3 to hollow interior 140-2 around a portion of the circumference, e.g., 100 to 180 degrees, of exterior surface 140-3.

Proximal end wall 142 of hub 128 may be configured as an insert, e.g., a plastic insert, to be inserted into a proximal opening in hub body 140, and fixedly attached to hub body 140, such as by adhesive, weld, etc. Proximal end wall 142 of hub 128 has a hole 142-1 centered on longitudinal axis 118 that is sized and shaped to slidably receive either of elongate needle 22 of biopsy device 12 or elongate needle 26 of trocar 14.

Distal end wall 144 of hub 128 may be configured as an end wall extension of hub body 140. Distal end wall 144 has a hole 144-1 that is sized and shaped to receive and mount proximal end portion 130-3 of elongate member 130, e.g., by over-mold, press fit, adhesive, weld, etc.

A seal member 146 is positioned adjacent to, and in sealing engagement with, distal end wall 144 in hollow interior 140-2 so as to form a seal with distal end wall 144 around hole 144-1. Seal member 146 has a hole 146-1 and a hole 146-2. Hole 146-1 of seal member 146 and hole 142-1 of proximal end wall 142 are aligned along longitudinal axis 118. Hole 146-1 of seal member 146 may be sized and shaped to slidably receive either of elongate needle 22 of biopsy device 12 or elongate needle 26 of trocar 14 in sealing engagement.

In seal member 146, hole 146-2 is centered on pushrod axis 130-7 and is radially spaced, relative to longitudinal axis 118, from the hole 146-1. Hole 146-2 is sized and shaped to slidably accommodate pushrod 132 in sealing engagement. When dual lumen coaxial introducer 116 is fully assembled, distal portion 132-2 of pushrod 132 is slidably received and slidably resides in hole 146-2 of seal member 146 and in second lumen 130-2 of elongate member 130.

In the present embodiment, seal member 146 may be made in its entirety of an elastomer, e.g., rubber, to form a seal at hole 146-1 to engage the circumferential surface of the elongate needle, e.g., elongate needle 22 of biopsy device 12 or elongate needle 26 of trocar 14, and to form a seal at hole 146-2 to engage the circumferential surface of the distal portion 132-2 of pushrod 132. Alternatively, sealing at distal end wall 144 may be provided by discrete seal members, such as respective O-rings located in distal end wall 144 to form hole 146-1 and to form hole 146-2. Such sealing prevents fluids at the biopsy site from passing proximally into hub body 140.

Figure 10:
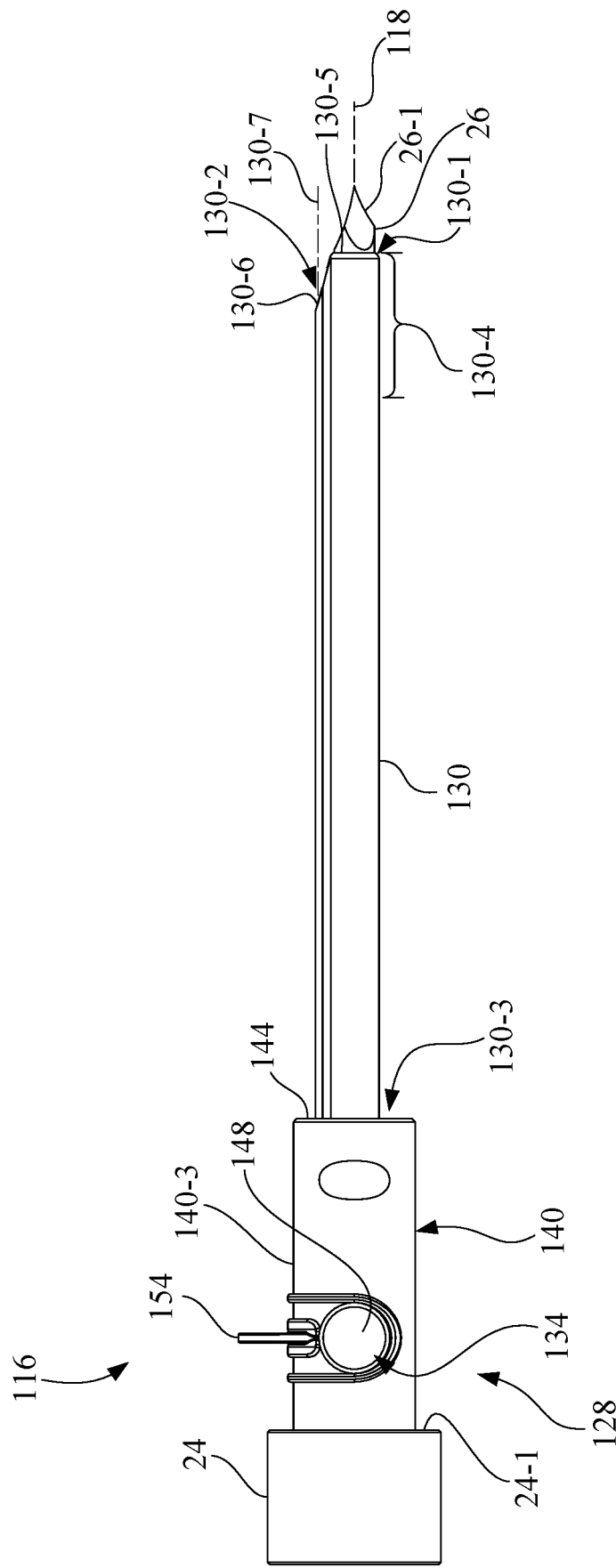
FIG. 10 is a side view of a configuration of components of FIG. 9, having the dual lumen coaxial introducer installed on the trocar biopsy device.

Referring to FIGS. 10, 11, and 14, actuator 134 is rotatably mounted to hub 128. Referring also to FIGS. 13, 13A, and 13B, actuator 134 is configured to be operable by a user to facilitate movement of pushrod 132 from retracted position 132-5 to extended position 132-6 to expel tissue marker 36 from second lumen 130-2. In the present embodiment, actuator 134 is configured as a rotary assembly having an actuator lever 148 attached to a cylindrical body 150.

Actuator lever 148 projects outwardly from the guide slot 140-4, and is movable along the guide slot 140-4 about longitudinal axis 118. Cylindrical body 150 is drivably connected to actuator lever 148.

Referring to FIGS. 3-14, cylindrical body 150 has a cylindrical hole 150-1 located on longitudinal axis 118 to slidably receive either of elongate needle 22 of biopsy device 12 or elongate needle 26 of trocar 14. Cylindrical body 150 has a proximal annular (radial) protrusion 150-2 that defines a proximal first bearing surface 150-3 and has a distal radial protrusion 150-4 defining a distal second bearing surface 150-5. Proximal first bearing surface 150-3 and distal second bearing surface 150-5 are rotatably received in the hollow interior 140-2 of the hub body 140. Cylindrical body 150 is restrained in hollow interior 140-2 of the hub body 140 from longitudinal movement along longitudinal axis 118, such as by proximal annular (radial) protrusion 150-2 and distal radial protrusion 150-4 being received in respective annular channels of hollow interior 140-2, or by being received between a pair of longitudinally spaced stops in hollow interior 140-2.

Referring to FIG. 14, cylindrical body 150 has an exterior longitudinally oriented spiral groove 150-6. Exterior longitudinally oriented spiral groove 150-6 is configured to drivably receive drive protrusion 132-4 of proximal portion 132-1 of pushrod 132.

Referring to FIG. 14, a rotation of actuator lever 148 about longitudinal axis 118 in a first rotational direction 152-1 results in a corresponding rotation of cylindrical body 150 in first rotational direction 152-1. Exterior longitudinally oriented spiral groove 150-6 converts the rotational motion in first rotational direction 152-1 to linear motion to move the pushrod 132 from retracted position 132-5 (see FIG. 13) to extended position 132-6 (see FIGS. 13A and 13B). A rotation of actuator lever 148 about longitudinal axis 118 in a second rotational direction 152-2, opposite first rotational direction 152-1, results in a corresponding rotation of cylindrical body 150 in second rotational direction 152-2. Exterior longitudinally oriented spiral groove 150-6 converts the rotational motion in second rotational direction 152-2 to linear motion to move pushrod 132 from extended position 132-6 to retracted position 132-5.

Referring to FIGS. 9-13 and 14, a safety insert 154 may be positioned in the guide slot 140-4 to prevent rotation of actuator lever 148 to until safety insert 154 is removed (see FIGS. 13B and 14).

Figure 15:
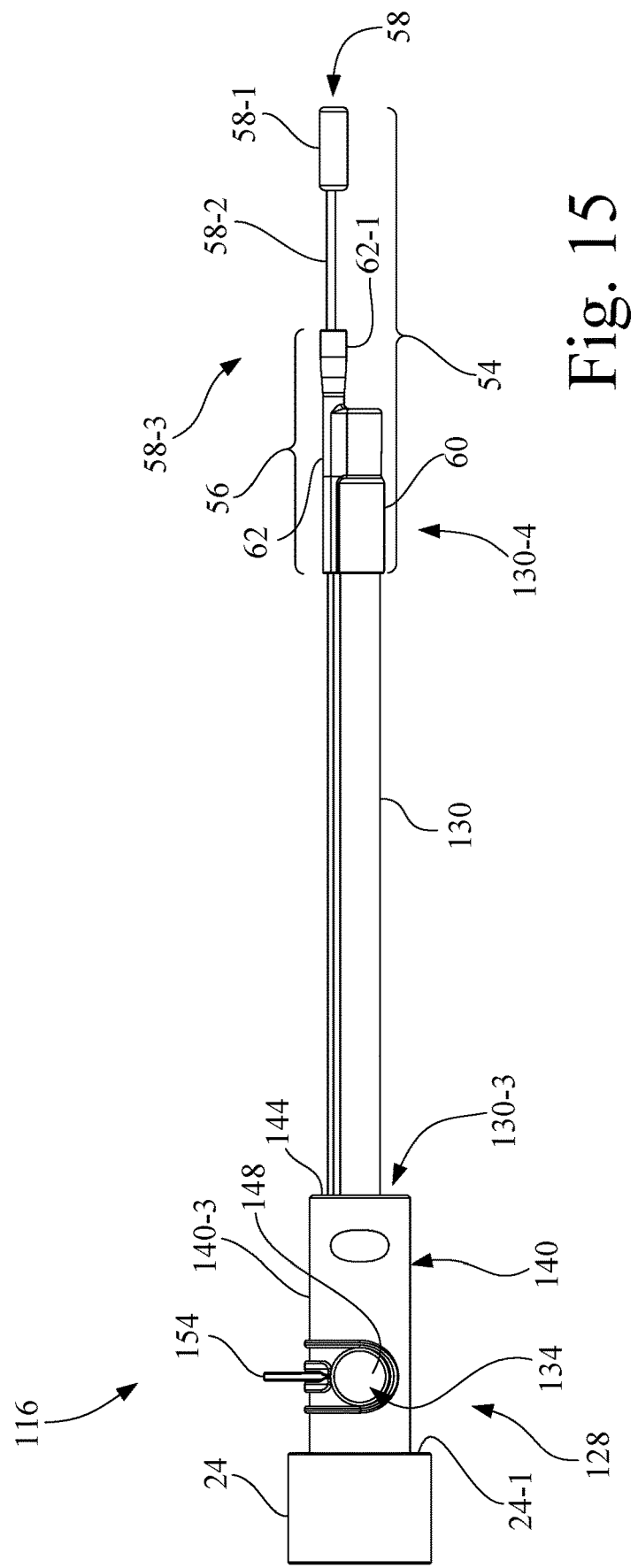
FIG. 15 is a side view of the configuration of the dual lumen coaxial introducer and the trocar of FIG. 10, with the marker loader of FIG. 8 installed on a distal end portion of the dual lumen coaxial introducer and having the safety insert of the marker loader removed.

Referring to FIG. 15 in conjunction with FIG. 10, biopsy system 110 may further include marker loader 54 configured to transfer tissue marker 36 from marker loader into marker recess 138 in second lumen 130-2 of elongate member 130 of dual lumen coaxial introducer 116. Marker loader 54 is described in detail above, and for brevity will not be repeated in its entirety here.

Referring also to FIG. 8 in conjunction with FIGS. 10 and 15, receptacle recess 60-1 of mounting portion 60 of marker loader 54 is configured to be received over distal end portion 130-4 of elongate member 130 to align lumen 62-2 of marker tube 62 of loader body 56 (see FIG. 8) with second lumen 130-2 of elongate member 130. In the present embodiment, distal end portion 130-4 of elongate member 130 has an external figure-8 transverse shape (see FIG. 12), and receptacle recess 60-1 of mounting portion 60 of loader body 56 has a corresponding internal figure-8 transverse shape (see FIG. 8) to slidably receive distal end portion 130-4 of elongate member 130 in a snug fit.

The operation of marker loader 54 for loading tissue marker 36 into marker recess 138 in second lumen 130-2 of elongate member 130 of dual lumen coaxial introducer 116 is the same as described above in loading tissue marker 36 into marker recess 38 in second lumen 30-2 of elongate member 30 of dual lumen coaxial introducer 16, and thus for brevity will not be repeated here. In summary, referring to FIG. 15, plunger 58 of marker loader 54 may be slid in marker tube 62 in a direction toward marker recess 138 (see FIG. 13) in second lumen 130-2 of elongate member 130 so as to load tissue marker 36 in marker recess 138 in second lumen 130-2 of elongate member 130.

Figure 16:
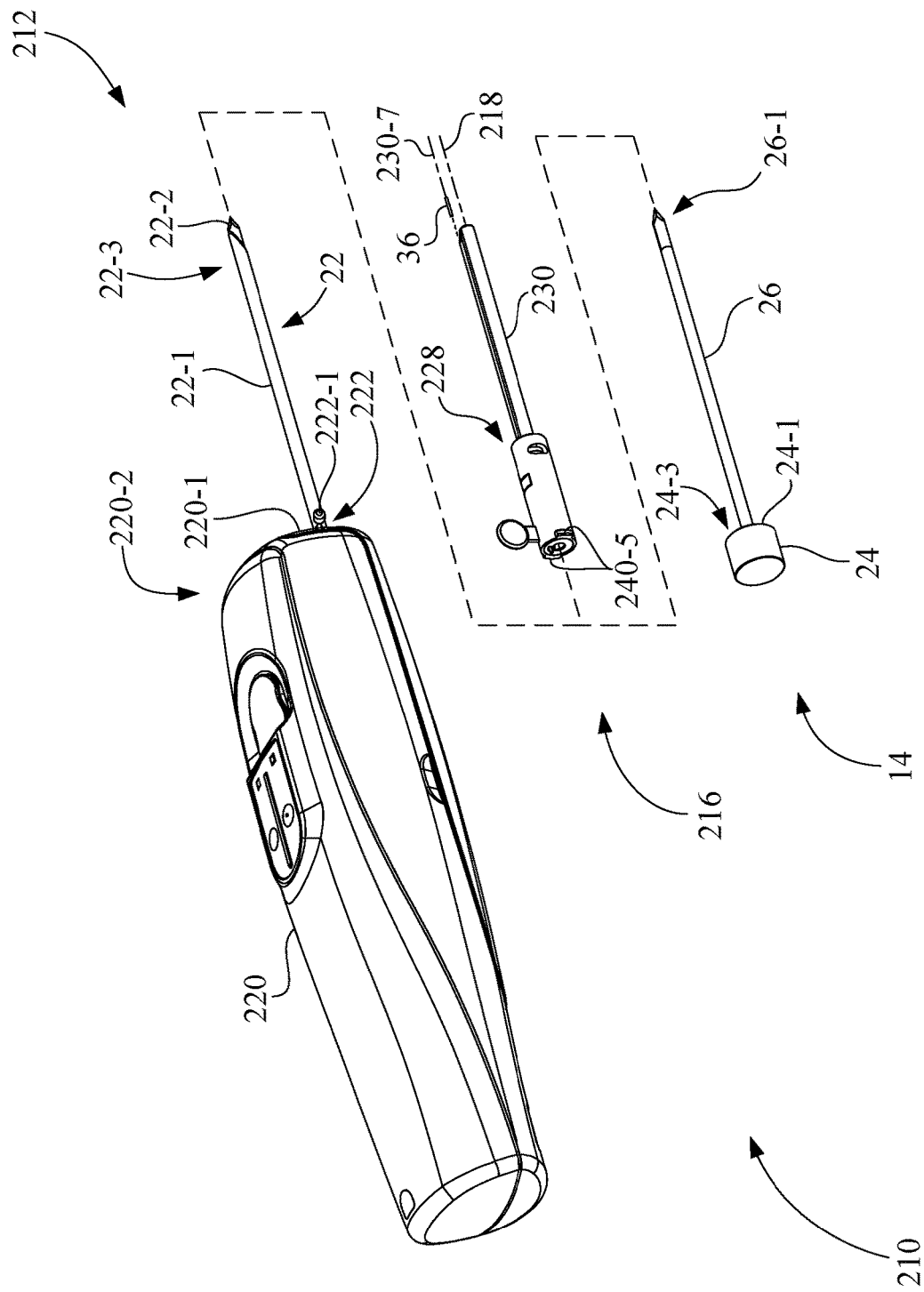
FIG. 16 is a perspective view of a biopsy system having a sample-taking biopsy device, a trocar biopsy device, and a dual lumen coaxial introducer, in accordance with another embodiment of the present invention.
Figure 17:
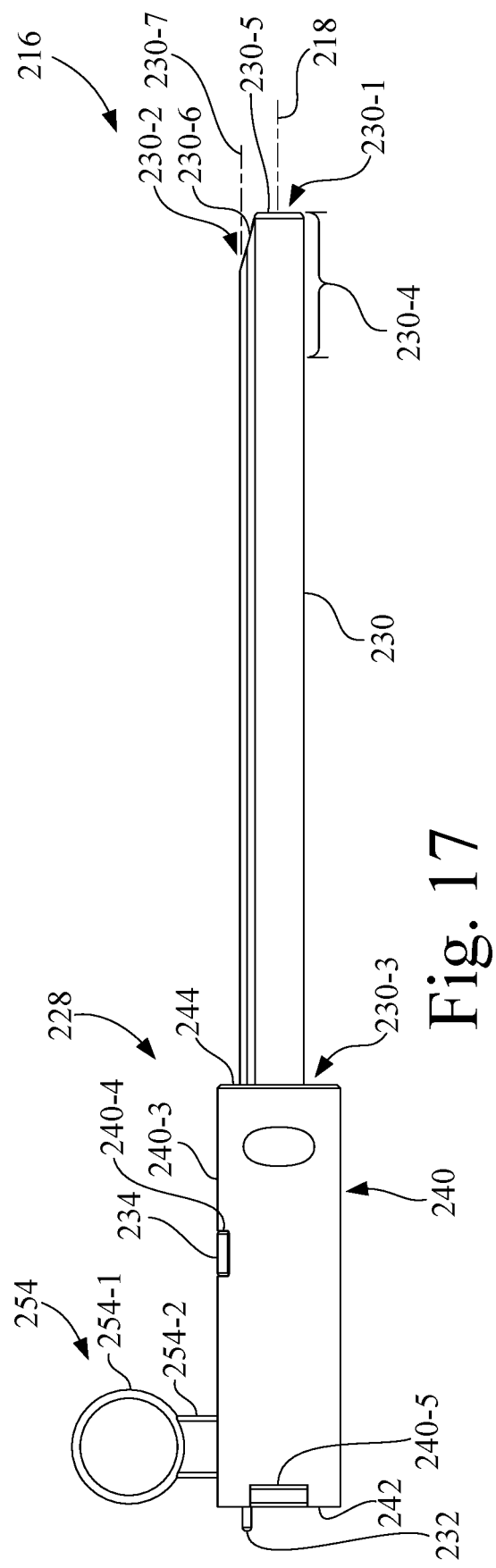
FIG. 17 is a side view of the dual lumen coaxial introducer of FIG. 16.
Figure 18:
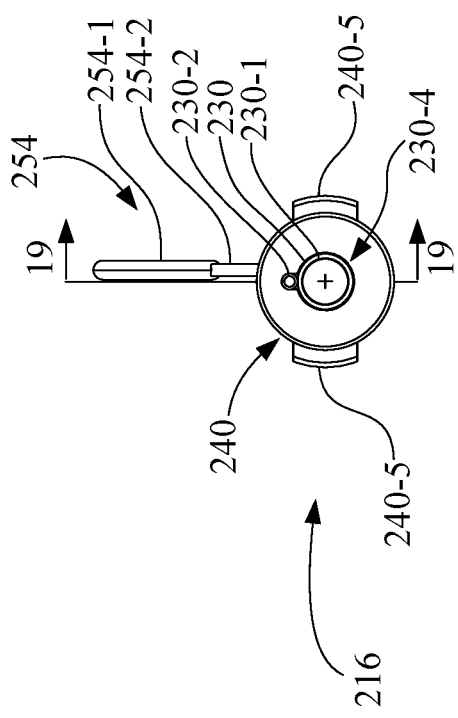
FIG. 18 is an end view of the dual lumen coaxial introducer of FIG. 17.

FIG. 16 shows a biopsy system 210 having a dual lumen coaxial introducer in accordance with another embodiment of the present invention. More particularly, biopsy system 210 includes a biopsy device 212; biopsy device (trocar) 14, as described above; and a dual lumen coaxial introducer 216 configured in accordance with an aspect of the present invention.

As depicted, dual lumen coaxial introducer 216 is configured to receive either of biopsy device 212 or trocar 14 along a longitudinal axis 218 of dual lumen coaxial introducer 216. In addition, in accordance with an aspect of the present invention, dual lumen coaxial introducer 216 is configured with a dedicated marker lumen to carry the pre-loaded tissue marker 36, and to eject tissue marker 36 at a site within a patient, such as a biopsy site, without necessitating removal or change in configuration of the installed biopsy device, e.g., biopsy device 212 or trocar 14.

Biopsy device 212, which may be based on the Finesse™ brand biopsy device available from C.R. Bard, Inc., has a device body 220 and an elongate needle 22 that extends distally from device body 220. Elongate needle 22 may form a portion of a releasable biopsy probe, as is known in the art, and in the context of the present application, a housing of such releasable biopsy probe is considered to be part of device body 220. Elongate needle 22 may include a cutting cannula 22-1 and a stylet 22-2. Elongate needle 22 has a cutting distal end 22-3 to perform tissue piercing and cutting in performing a biopsy procedure in a manner known in the art. Device body 220 contains driving components that couple to elongate needle 22 for performing a biopsy procedure in a manner as is known in the art.

Device body 220 includes a mounting portion 220-1 for releasable attachment to dual lumen coaxial introducer 216. In the present embodiment, mounting portion 220-1 may be configured as a threaded cylinder for receiving a proximal end, e.g., one-quarter turn tabs 240-5, of dual lumen coaxial introducer 216, to accommodate releasable attachment. Likewise, mounting portion 24-1 of trocar body 24 of trocar 14 may include a threaded cylinder 24-3 to receive the one-quarter turn tabs 240-5 of dual lumen coaxial introducer 216, to accommodate releasable attachment.

In the present embodiment, device body 220 further includes an actuator 222 for operating dual lumen coaxial introducer 216 to deliver tissue marker 36 to a delivery site, e.g., a biopsy site, in a patient. More particularly, actuator 222 is mounted to biopsy device 212 near a distal end 220-2 of device body 220. Actuator 222 includes an actuator button 222-1 that is configured, e.g., as a pushbutton, to be operable by a user to operate dual lumen coaxial introducer 216 to expel tissue marker 36 from a marker lumen of dual lumen coaxial introducer 216, as described in more detail below.

Referring also to FIGS. 17-22, dual lumen coaxial introducer 216 includes a hub 228, an elongate member 230, a pushrod 232, and an engagement member 234. As shown in FIG. 19, dual lumen coaxial introducer 216 is configured to carry tissue marker 36.

Hub 228, having one-quarter turn tabs 240-5, is configured for releasable attachment to either of device body 220 of biopsy device 212 or trocar body 24 of trocar 14.

In the present embodiment, elongate member 230 has a first lumen 230-1, a second lumen 230-2, a proximal end portion 230-3, a distal end portion, 230-4, a blunt distal end 230-5, and a beveled distal end 230-6. First lumen 230-1 defines longitudinal axis 218, and distally terminates at blunt distal end 230-5. Second lumen 230-2 defines a pushrod axis 230-7, and distally terminates at beveled distal end 230-6.

Proximal end portion 230-3 of elongate member 230 is fixedly attached to hub 228, e.g., by over-mold, press fit, adhesive, weld, etc. First lumen 230-1 is sized and shaped to slidably receive either of elongate needle 22 of biopsy device 212 or elongate needle 26 of trocar 14. Second lumen 230-2 is sized and shaped to slidably receive pushrod 232 for movement along pushrod axis 230-7 and to carry tissue marker 36 for future deployment (see FIG. 19). Elongate member 230 may be formed from two joined cannula, as shown for example in FIGS. 17-20, respectively having first lumen 230-1 and second lumen 230-2. Alternatively, elongate member 230 may be formed as a single elongate member having two bores respectively corresponding to first lumen 230-1 and second lumen 230-2.

Pushrod 232 is located in second lumen 230-2 of elongate member 230 for sliding movement along pushrod axis 230-7. Pushrod 232 may be formed as a unitary member that has a proximal portion 232-1, a distal portion 232-2, a distal end surface 232-3, and a flange 232-4. Flange 232-4 is interposed between proximal portion 232-1 and distal portion 232-2. Distal portion 232-2 is slidably received in second lumen 230-2 of elongate member 230. Pushrod 232 is movable between a retracted position 232-5 shown in FIG. 19 and an extended position 232-6 shown in FIGS. 19A and 19B.

Actuator button 222-1 is configured, e.g., as a pushbutton, to be operable by a user to facilitate movement of the pushrod 232 from retracted position 232-5 (FIG. 19) to extended position 232-6 (FIGS. 19A and 19B) to expel tissue marker 36 from second lumen 230-2 of dual lumen coaxial introducer 216. Referring to FIG. 19, in retracted position 232-5, distal end surface 232-3 of pushrod 232 is spaced away from beveled distal end 230-6 of elongate member 230 to define a marker recess 238 in second lumen 230-2 of elongate member 230 that will receive and carry tissue marker 36. With tissue marker 36 positioned in marker recess 238 of second lumen 230-2, when pushrod 232 is moved from retracted position 232-5 (FIG. 19) to extended position 232-6 (FIGS. 19A and 19B), tissue marker 36 is expelled from second lumen 230-2 and deposited at the biopsy site.

Referring to FIGS. 19 and 19B, hub 228 includes a hub body 240, a proximal end wall 242, and a distal end wall 244. Hub body 240 has a side wall 240-1 that defines a hollow interior 240-2 and an exterior surface 240-3. Hub body 240 has a latch slot 240-4 (see also FIG. 20) that extends through side wall 240-1 from exterior surface 240-3 to hollow interior 240-2. Hub body 240 may further include one-quarter turn tabs 240-5 (see FIG. 20), which are sized and shaped for releasable engagement with either of mounting portion 220-1 of biopsy device 212 or mounting portion 24-1 of trocar body 24 of trocar 14. Proximal end wall 242 and distal end wall 244 are spaced apart along the longitudinal axis 218.

Figure 20:
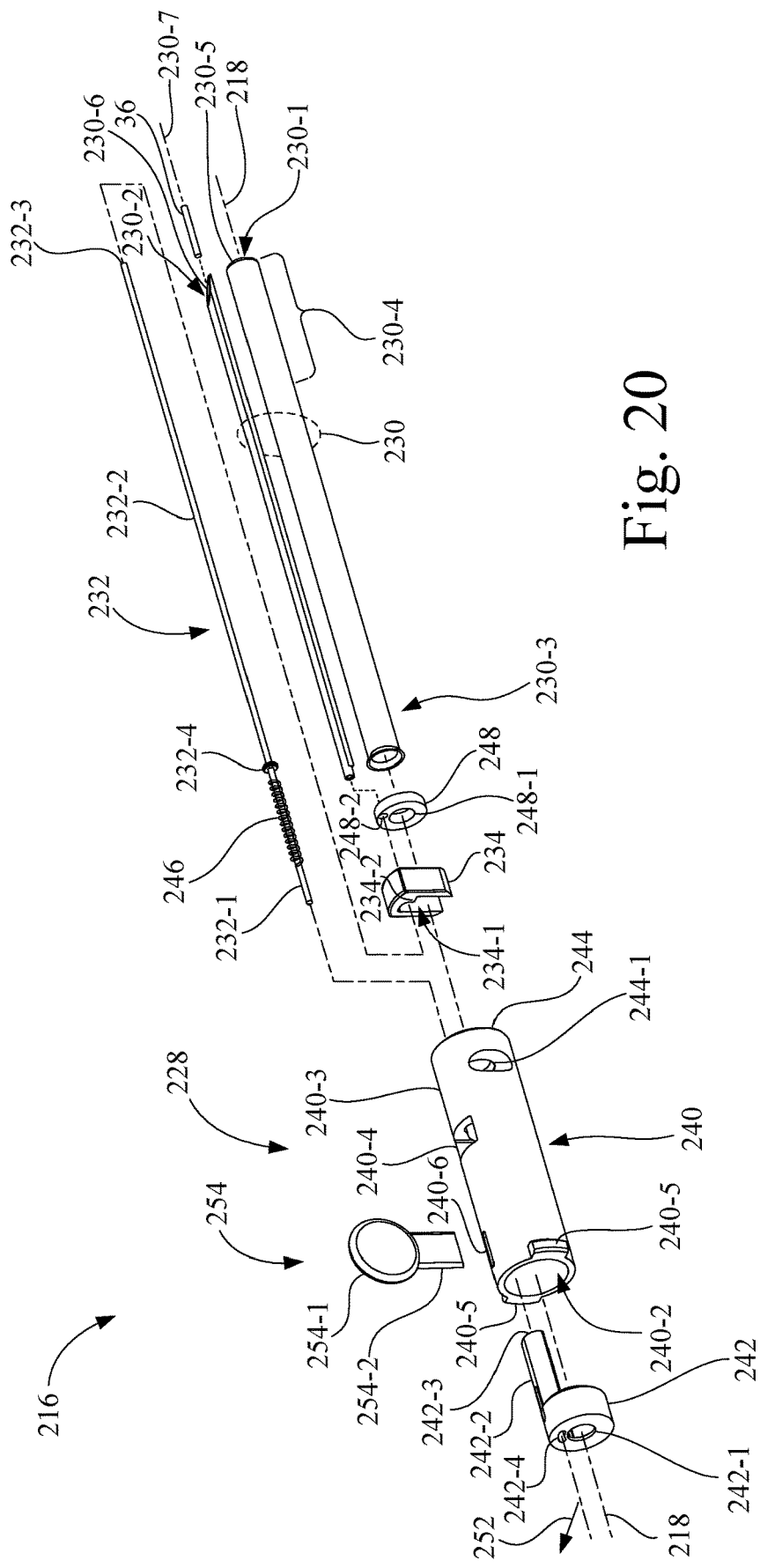
FIG. 20 is an exploded view of the dual lumen coaxial introducer of FIGS. 17 and 18.
Figure 21:
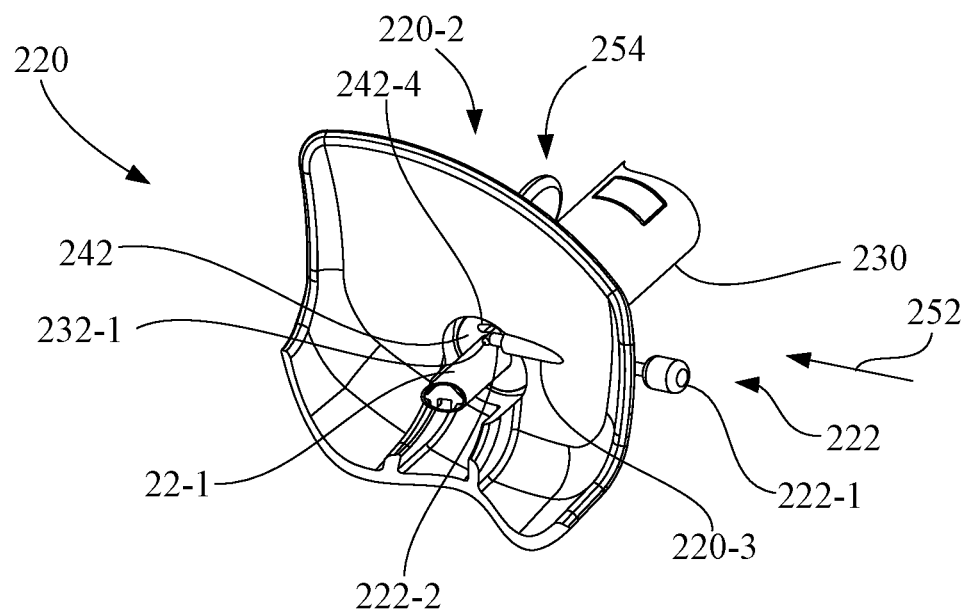
FIG. 21 is an enlarged perspective view of a distal portion of the biopsy device of FIG. 16, showing the actuator button and linkage, with the linkage engaged with a lateral surface of the pushrod.

Referring to FIGS. 19 and 20, proximal end wall 242 of hub 228 may be configured as an insert, e.g., a plastic insert, to be inserted into a proximal opening in hub body 240, and is fixedly attached to hub body 240, such as by adhesive, weld, etc. Proximal end wall 242 of hub 228 has a hole 242-1 centered on longitudinal axis 218 sized and shaped to slidably receive either of elongate needle 22 of biopsy device 212 or elongate needle 26 of trocar 14. Proximal end wall 242 also includes a distally extending arm 242-2 that defines a spring seat 242-3. Referring to FIGS. 20 and 21, proximal end wall 242 includes a slotted hole 242-4 to receive proximal portion 232-1 of pushrod 232.

Distal end wall 244 of hub 228 may be configured as an end wall extension of hub body 240. Distal end wall 244 has a hole 244-1 sized and shaped to receive and mount proximal end portion 230-3 of elongate member 230, e.g., by over-mold, press fit, adhesive, weld, etc.

A spring 246, e.g., a coil spring, is positioned over proximal portion 232-1 of pushrod 232, and is positioned between spring seat 242-3 of proximal end wall 242 of hub 228 and flange 232-4 of pushrod 232. When pushrod 232 is in retracted position 232-5 (see FIG. 19), spring 246 is in a compressed state and when pushrod 232 is in extended position 232-6 (see FIG. 19B), spring 246 is relaxed from the compressed state, i.e., is decompressed to an extended condition.

Referring to FIG. 20, with respect to FIG. 19, engagement member 234 is positioned in latch slot 240-4 of hub body 240, e.g., in a snug fit, to extend into the hollow interior 240-2 of hub body 240. In the present embodiment, engagement member 234 may be formed, for example, as a downwardly facing U-shaped structure. Engagement member 234 has a passage 234-1 defined by the U-shaped structure, in which pushrod 232 movably resides. Engagement member 234 also defines a proximal lateral engagement surface 234-2 for engagement with flange 232-4 of pushrod 232 (see FIGS. 19 and 20).

Figure 22:
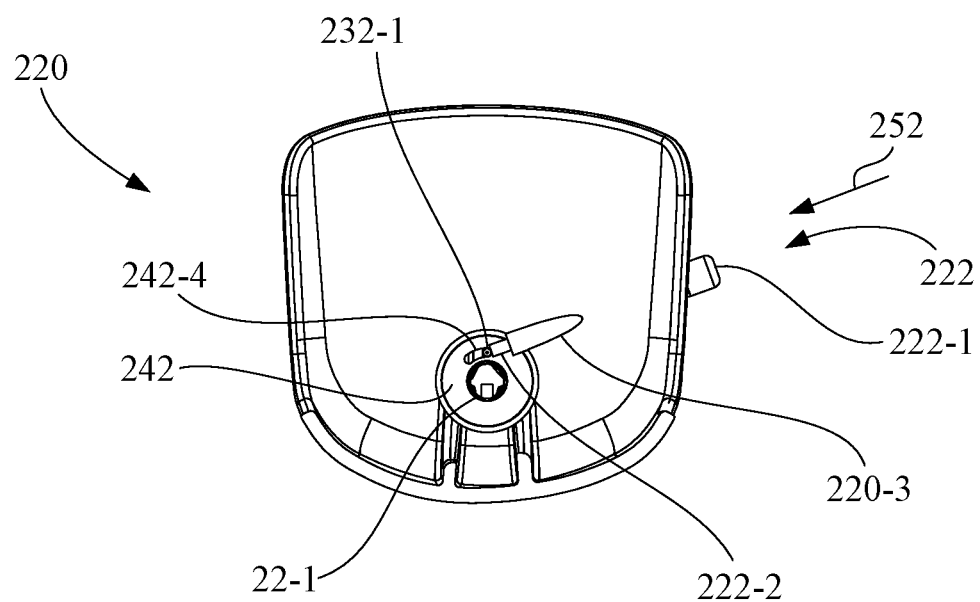
FIG. 22 is an enlarged rear view of a distal portion of the biopsy device of FIG. 16, showing the actuator button and linkage, with the linkage engaged with a lateral surface of the pushrod.

Referring also to FIGS. 21 and 22, actuator 222 is configured, e.g., through depressing actuator button 222-1, to move proximal portion 232-1 of pushrod 232 laterally, so as to disengage flange 232-4 of pushrod 232 from proximal lateral engagement surface 234-2 of engagement member 234, so as to facilitate movement of pushrod 232 from the retracted position 232-5 (see FIG. 19) and an extended position 232-6 (see FIGS. 19A and 19B) through the release of spring 246 from the compressed state.

In particular, actuator 222 further includes a linkage 222-2 that is drivably interposed between actuator button 222-1 of biopsy device 212 and proximal portion 232-1 of pushrod 232 of dual lumen coaxial introducer 216. Device body 220 includes a distal channel 220-3 for slidably receiving linkage 222-2 therethrough. In operation, a user applies a pressing force to actuator button 222-1 in direction 252, so as to depress actuator button 222-1, which in turn moves linkage 222-2 in direction 252 to engage proximal portion 232-1 of pushrod 232. This movement of linkage 222-2 in direction 252 in turn moves proximal portion 232-1 of pushrod 232 laterally in slotted hole 242-4 of proximal end wall 242 in direction 252. This lateral movement of proximal portion 232-1 of pushrod 232 in slotted hole 242-4 of proximal end wall 242 in direction 252 moves flange 232-4 of pushrod 232 laterally to disengage flange 232-4 of pushrod 232 from proximal lateral engagement surface 234-2 of engagement member 234 (see also FIGS. 19, 19B, and 20). Once flange 232-4 of pushrod 232 is moved laterally to disengage flange 232-4 of pushrod 232 from proximal lateral engagement surface 234-2 of engagement member 234, flange 232-4 of pushrod 232 no longer restrains spring 246 in the compressed state. As spring 246 decompresses, pushrod 232 is moved by the spring force exerted by spring 246 against flange 232-4 from retracted position 232-5 (see FIG. 19) to extended position 232-6 (see FIGS. 19A and 19B).

Referring to FIG. 20, hub body 240 may further include safety slot 240-6, which extends through side wall 240-1 from exterior surface 240-3 to hollow interior 240-2 (see also FIG. 19). Safety slot 240-6 is configured to receive a safety insert 254 (see FIGS. 16-19, 19B, and 20). Safety insert 254 has a handle portion 254-1 and a distal portion 254-2. To effect a safety condition, safety insert 254 is inserted, i.e., in a sliding action, into safety slot 240-6 such that distal portion 254-2 is positioned adjacent proximal portion 232-1 of pushrod 232, between side wall 240-1 of hub body 240 of hub 228 and proximal portion 232-1 of pushrod 232. With distal portion 254-2 of safety insert 254 positioned adjacent proximal portion 232-1 of pushrod 232, distal portion 254-2 of safety insert 254 prevents lateral movement of proximal portion 232-1 of pushrod 232 to until safety insert 254 is removed. In other words, distal portion 254-2 of safety insert 254 prevents flange 232-4 of pushrod 232 from being moved laterally so as to disengage flange 232-4 of pushrod 232 from proximal lateral engagement surface 234-2 of engagement member 234, thereby preventing release of spring 246 from the compressed state to until safety insert 254 is withdrawn.

Referring again to FIGS. 19 and 20, dual lumen coaxial introducer 216 may include a seal member 248 that is positioned adjacent to, and in sealing engagement with, distal end wall 244 in hollow interior 240-2 so as to form a seal with distal end wall 244 around hole 244-1. Seal member 248 has a hole 248-1 and a hole 248-2. Hole 248-1 of seal member 248 and hole 242-1 of proximal end wall 242 are aligned along longitudinal axis 218. Hole 248-1 of seal member 248 is sized and shaped to slidably receive either of elongate needle 22 of biopsy device 212 or elongate needle 26 of trocar 14 in sealing engagement.

In seal member 248, hole 248-2 is centered on pushrod axis 230-7 and is radially spaced, relative to longitudinal axis 218, from the hole 248-1. Hole 248-2 is sized and shaped to slidably accommodate pushrod 232 in sealing engagement. When dual lumen coaxial introducer 216 is fully assembled, distal portion 232-2 of pushrod 232 is slidably received and slidably resides in hole 248-2 of seal member 248 and in second lumen 230-2 of elongate member 230.

In the present embodiment, seal member 248 may be made in its entirety of an elastomer, e.g., rubber, to form a seal at hole 248-1 to engage the circumferential surface of the elongate needle, e.g., elongate needle 22 of biopsy device 212 or elongate needle 26 of trocar 14, and to form a seal at hole 248-2 to engage the circumferential surface of the distal portion 232-2 of pushrod 232. Alternatively, sealing at distal end wall 244 may be provided by discrete seal members, such as respective O-rings located in distal end wall 244 to form hole 248-1 and to form hole 248-2. Such sealing prevents fluids at the biopsy site from passing proximally into hub body 240.

Figure 23:
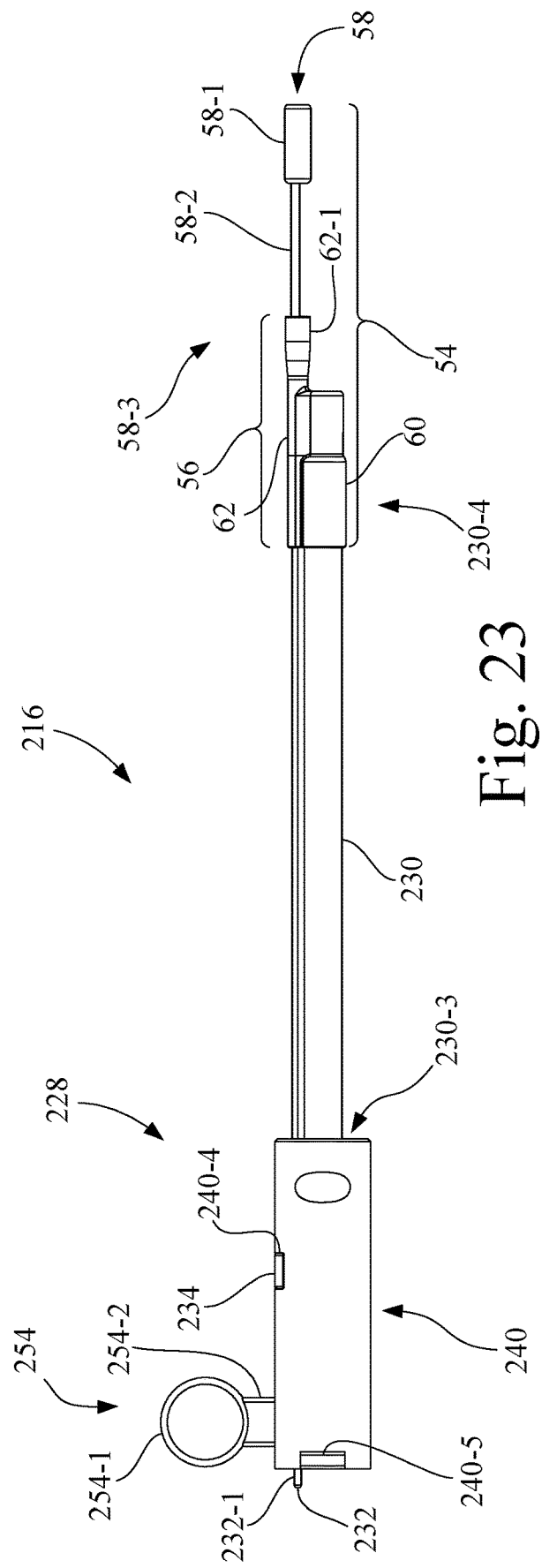
FIG. 23 is a side view of the configuration of the dual lumen coaxial introducer of FIG. 17, with the marker loader of FIG. 8 installed on a distal end portion of the dual lumen coaxial introducer and having the safety insert of the marker loader removed.

Referring to FIG. 23 in conjunction with FIG. 19, biopsy system 210 may further include marker loader 54, described above with respect to FIG. 8, which is configured to load tissue marker 36 into marker recess 238 in second lumen 230-2 of elongate member 230 of dual lumen coaxial introducer 216. Marker loader 54 is described in detail above, and for brevity will not be repeated in its entirety here.

Referring also to FIG. 8, receptacle recess 60-1 of mounting portion 60 of marker loader 54 is configured to be received over distal end portion 230-4 of elongate member 230 to align lumen 62-2 of marker tube 62 of loader body 56 (see FIG. 8) with second lumen 230-2 of elongate member 230 (see FIG. 19). In the present embodiment, distal end portion 230-4 of elongate member 230 has an external figure-8 transverse shape (see FIG. 18), and receptacle recess 60-1 of mounting portion 60 of loader body 56 has a corresponding internal figure-8 transverse shape (see FIG. 8) to slidably receive distal end portion 230-4 of elongate member 230 in a snug fit.

The operation of marker loader 54 for loading tissue marker 36 into marker recess 238 in second lumen 230-2 of elongate member 230 of dual lumen coaxial introducer 216 is the same as described above in loading tissue marker 36 into marker recess 38 in second lumen 30-2 of elongate member 30 of dual lumen coaxial introducer 16, and thus for brevity will not be repeated here. In summary, referring to FIG. 23, plunger 58 of marker loader 54 may be slid in marker tube 62 in a direction toward marker recess 238 in second lumen 230-2 of elongate member 230 (see FIG. 19) so as to load tissue marker 36 in marker recess 238 in second lumen 230-2 of elongate member 230.

The following items also relate to the invention:

In one form, the invention relates to a dual lumen coaxial introducer for use with an elongate needle. The dual lumen coaxial introducer includes a hub, an elongate member, and a pushrod. The elongate member has a first lumen, a second lumen, a proximal end portion, and a distal end. The proximal end portion is fixedly attached to the hub, the first lumen defining a longitudinal axis and configured to slidably receive the elongate needle. The pushrod is located in the second lumen. The pushrod has a distal end surface. The pushrod is movable between a retracted position and an extended position. The introducer is configured such that, in the retracted position, the distal end surface of the pushrod is spaced away from the distal end of the elongate member to define a marker recess in the second lumen for carrying a tissue marker for delivery to a delivery site.

The dual lumen coaxial introducer may include an actuator mounted to the hub. The actuator may be configured to be operable by a user to facilitate movement of the pushrod from the retracted position to the extended position to expel the tissue marker from the second lumen.

In any embodiment, the hub may include a hub body having a side wall, a proximal end wall, and a distal end wall. The side wall defines a hollow interior and an exterior surface, and has a guide channel that extends through the side wall from the exterior surface to the hollow interior. The proximal end wall has a first hole, and the distal end wall has a second hole. The first hole of the proximal end wall is configured to slidably receive the elongate needle and the second hole of the distal end wall is configured to receive and mount the proximal end portion of the elongate member.

In any embodiment, a seal member may be positioned adjacent to the distal end wall in the hollow interior of the hub body. The seal member has a third hole and a fourth hole. The first hole of the proximal end wall and the third hole of the seal member are aligned along the longitudinal axis and configured to slidably receive the elongate needle. The fourth hole is radially spaced from the third hole, with the pushrod slidably residing in the fourth hole.

The proximal end wall of the hub may be configured to define a spring seat. The pushrod has a proximal portion, a distal portion, and a flange interposed between the proximal portion and the distal portion. The distal portion is slidable within the second lumen of the elongate member. A spring is positioned between the spring seat of the proximal end wall of the hub and the flange of the pushrod. The introducer is configured such that when the pushrod is in the retracted position, the spring is in a compressed state and when the pushrod is in the extended position, the spring is relaxed from the compressed state. The actuator may be configured as a button assembly having an actuator button attached to an engagement member. The engagement member has a passage in which the pushrod movably resides. The engagement member is positioned in the guide channel of the hub body to extend into the hollow interior of the hub body. The actuator button is positioned to project outwardly from the guide channel. The engagement member has a proximal engagement surface. The actuator button may be configured to move the engagement member in the guide channel from an engaged position to a release position. The introducer is configured such that when the pushrod is in the retracted position and the engagement member of the actuator is in the engaged position, the flange of the pushrod is engaged with the proximal engagement surface of the engagement member with the spring being in the compressed state. The introducer is configured such that when the user applies an external force to the actuator button of the actuator to move the engagement member to the release position, the proximal engagement surface of the engagement member is moved out of engagement with the flange of the pushrod to release the spring from the compressed state to move the pushrod from the retracted position to the extended position.

In the previously described embodiment, the introducer is configured such that the external force depresses the actuator button of the actuator in a direction toward the pushrod.

The seal member may be made of an elastomer.

A safety insert may be interposed between the actuator and the hub to prevent operation of the actuator to until the safety insert is removed.

A marker loader may be configured to load the tissue marker into the marker recess in the second lumen of the elongate member. The marker loader includes a loader body having a mounting portion having a receptacle recess, and has a marker tube for carrying the tissue marker to be positioned in the marker recess in the second lumen of the elongate member. The receptacle recess of the mounting portion may be configured to be received over a distal end portion of the elongate member to align the marker tube of the loader body with the second lumen of the elongate member. The marker loader has a plunger having a head portion and a shaft portion. The shaft portion is slidably received in the marker tube. The plunger may be configured to move between a holding position and a loaded position to deliver the tissue marker from the marker tube of the loader body to the marker recess in the second lumen of the elongate member.

The distal end portion of the elongate member may have an external figure-8 transverse shape, and the receptacle recess of the mounting portion of the loader body may have an internal figure-8 transverse shape to slidably receive the distal end portion of the elongate member in a snug fit.

A safety insert may be interposed between the head portion of the plunger and the loader body and configured to prevent operation of the plunger of the marker loader to until the safety insert is removed.

In another embodiment of the dual lumen coaxial introducer, the hub may include a hub body having a side wall, a proximal end wall, and a distal end wall. The side wall defines a hollow interior and an exterior surface, and has a guide slot that extends through the side wall from the exterior surface to the hollow interior. The proximal end wall has a first hole and the distal end wall has a second hole. The first hole is configured to slidably receive the elongate needle of the biopsy device and the second hole of the distal end wall is configured to receive and mount the proximal end portion of the elongate member. The proximal end wall and the distal end wall are spaced apart along the longitudinal axis.

In this embodiment, the actuator has an actuator lever that projects outwardly from the guide slot. The actuator lever is movable along the guide slot about the longitudinal axis.

In this embodiment, the pushrod may have a proximal portion and a distal portion, and the proximal portion has a drive protrusion. The distal portion is slidably received in the second lumen of the elongate member. The actuator may further include a cylindrical body drivably connected to the actuator lever. The cylindrical body has a cylindrical hole located on the longitudinal axis to slidably receive the elongate needle of the biopsy device. The cylindrical body has a proximal annular protrusion that defines a proximal bearing surface and a distal radial protrusion defining a second bearing surface. The first bearing surface and the second bearing surface are rotatably received in the hollow interior of the hub body. The cylindrical body has an exterior longitudinally oriented spiral groove. The exterior longitudinally oriented spiral groove is configured to drivably receive the drive protrusion of the proximal portion of the pushrod.

The introducer is configured such that a rotation of the actuator lever about the longitudinal axis in a first rotational direction results in a corresponding rotation of the cylindrical body in the first rotational direction. The introducer is configured such that the exterior longitudinally oriented spiral groove converts rotational motion in the first rotational direction to linear motion to move the pushrod from the retracted position to the extended position. The introducer is configured such that a rotation of the actuator lever about the longitudinal axis in a second rotational direction results in a corresponding rotation of the cylindrical body in the second rotational direction. The introducer is configured such that the exterior longitudinally oriented spiral groove converts rotational motion in the second rotational direction to linear motion to move the pushrod from the extended position to the retracted position.

A seal member may be made of an elastomer, and may form a seal between the distal end wall and a circumferential surface of the elongate needle.

The seal member may also form a seal between the distal end wall and a circumferential surface of the distal portion of the pushrod.

A safety insert may be positioned in the guide slot to prevent rotation of the actuator lever to until the safety insert is removed.

A marker loader may be configured to load the tissue marker into the marker recess in the second lumen of the elongate member. The marker loader includes a loader body having a mounting portion having a receptacle recess, and having a marker tube for carrying the tissue marker to be positioned in the marker recess in the second lumen of the elongate member. The receptacle recess of the mounting portion is configured to be received over a distal end portion of the elongate member to align the marker tube with the second lumen of the elongate member. The marker loader includes a plunger having a head portion and a shaft portion. The shaft portion is slidably received in the marker tube. The plunger is configured to move between a holding position and a loaded position to deliver the tissue marker from the marker tube of the loader body to the marker recess in the second lumen of the elongate member.

The distal end portion of the elongate member may have an external figure-8 transverse shape, and the receptacle recess of the mounting portion of the loader body may have an internal figure-8 transverse shape to slidably receive the distal end portion of the elongate member in a snug fit.

A safety insert may be interposed between the head portion of the plunger and the loader body to prevent operation of the plunger of the marker loader to until the safety insert is removed.

The safety insert may include a channel that laterally slides over the shaft of the plunger.

In another form, the invention relates to a biopsy system having a biopsy device and a dual lumen coaxial introducer in accordance with any of the embodiments described above. The biopsy device has a device body and an elongate needle that extends distally from the device body. The elongate needle has a cutting distal end. The dual lumen coaxial introducer may be one of the introducers defined above, and may include a hub, an elongate member, and a pushrod. The hub is configured for releasable attachment to the biopsy device. The elongate member has a first lumen, a second lumen, a proximal end portion, and a distal end. The proximal end portion is fixedly attached to the hub. The first lumen defines a longitudinal axis and is configured to slidably receive the elongate needle of the biopsy device. The pushrod is located in the second lumen. The pushrod has a distal end surface. The pushrod is movable between a retracted position and an extended position, wherein in the retracted position, the distal end surface of the pushrod is spaced away from the distal end of the elongate member to define a marker recess in the second lumen for carrying a tissue marker for delivery to a delivery site.

In an embodiment of the biopsy system, an actuator may be mounted to the hub. The actuator may be configured to be operable by a user to facilitate movement of the pushrod from the retracted position to the extended position to expel the tissue marker from the second lumen.

The hub may include a hub body having a side wall, a proximal end wall, and a distal end wall. The side wall defines a hollow interior and an exterior surface, and may have a guide channel that extends through the side wall from the exterior surface to the hollow interior. The proximal end wall has a first hole, and the distal end wall has a second hole. The first hole of the proximal end wall is configured to slidably receive the elongate needle and the second hole of the distal end wall is configured to receive and mount the proximal end portion of the elongate member.

A seal member may be positioned adjacent to the distal end wall in hollow interior of the hub body. The seal member has a third hole and a fourth hole. The first hole of the proximal end wall and the third hole of the seal member are aligned along a longitudinal axis and configured to slidably receive the elongate needle. The fourth hole is radially spaced from the third hole, with the pushrod slidably residing in the fourth hole.

The seal member may be made of an elastomer.

The proximal end wall of the hub may be configured to define a spring seat. The pushrod may have a proximal portion, a distal portion, and a flange interposed between the proximal portion and the distal portion. The distal portion is slidable within the second lumen of the elongate member. A spring is positioned between the spring seat of the proximal end wall of the hub and the flange of the pushrod, wherein the system is configured such that when the pushrod is in the retracted position, the spring is in a compressed state and when the pushrod is in the extended position, the spring is relaxed from the compressed state. The actuator may be configured as a button assembly having an actuator button attached to an engagement member. The engagement member has a passage in which the pushrod movably resides. The engagement member is positioned in the guide channel of the hub body to extend into the hollow interior of the hub body. The actuator button may be positioned to project outwardly from the guide channel. The engagement member has a proximal engagement surface. The actuator button is configured to move the engagement member in the guide channel from an engaged position to a release position. The system is configured such that when the pushrod is in the retracted position and the engagement member of the actuator is in the engaged position, the flange of the pushrod is engaged with the proximal engagement surface of the engagement member with the spring being in the compressed state, and when the user applies an external force to the actuator button of the actuator to move the engagement member to the release position, the proximal engagement surface of the engagement member is moved out of engagement with the flange of the pushrod to release the spring from the compressed state to move the pushrod from the retracted position to the extended position.

The system is configured such that the external force may depress the actuator button of the actuator in a direction toward the pushrod.

A safety insert may be interposed between the actuator and the hub to prevent operation of the actuator to until the safety insert is removed.

A marker loader may be configured to load the tissue marker into the marker recess in the second lumen of the elongate member. The marker loader may include a loader body having a mounting portion having a receptacle recess, and having a marker tube for carrying the tissue marker to be positioned in the marker recess in the second lumen of the elongate member. The receptacle recess of the mounting portion may be configured to be received over a distal end portion of the elongate member to align the marker tube with the second lumen of the elongate member. The marker loader may include a plunger having a head portion and a shaft portion. The shaft portion is slidably received in the marker tube. The plunger is configured to move between a holding position and a loaded position to deliver the tissue marker from the marker tube of the loader body to the marker recess in the second lumen of the elongate member.

The distal end portion of the elongate member may have an external figure-8 transverse shape, and the receptacle recess of the mounting portion of the loader body may have an internal figure-8 transverse shape to slidably receive the distal end portion of the elongate member in a snug fit.

A safety insert may be interposed between the head portion of the plunger and the loader body to prevent operation of the plunger of the marker loader to until the safety insert is removed.

In another embodiment of the dual lumen coaxial introducer, the hub may include a hub body having a side wall, a proximal end wall, and a distal end wall. The side wall defines a hollow interior and an exterior surface, and having a guide slot that extends through the side wall from the exterior surface to the hollow interior. The proximal end wall has a first hole and the distal end wall having a second hole. The first hole is configured to slidably receive the elongate needle of the biopsy device and the second hole of the distal end wall is configured to receive and mount the proximal end portion of the elongate member. The proximal end wall and the distal end wall are spaced apart along the longitudinal axis. The actuator may have an actuator lever that projects outwardly from the guide slot. The actuator lever is movable along the guide slot about the longitudinal axis.

The pushrod may have a proximal portion and a distal portion. The proximal portion has a drive protrusion. The distal portion is slidably received in the second lumen of the elongate member. The actuator may further include a cylindrical body drivably connected to the actuator lever. The cylindrical body has a cylindrical hole located on the longitudinal axis to slidably receive the elongate needle of the biopsy device. The cylinder has a proximal annular protrusion that defines a proximal bearing surface and a distal radial protrusion defining a second bearing surface. The first bearing surface and the second bearing surface are rotatably received in the hollow interior of the hub body. The cylindrical body has an exterior longitudinally oriented spiral groove. The exterior longitudinally oriented spiral groove is configured to drivably receive the drive protrusion of the proximal portion of the pushrod. The system is configured such that a rotation of the actuator lever about the longitudinal axis in a first rotational direction results in a corresponding rotation of the cylindrical body in the first rotational direction, the exterior longitudinally oriented spiral groove converting rotational motion in the first rotational direction to linear motion to move the pushrod from the retracted position to the extended position. The system is configured such that a rotation of the actuator lever about the longitudinal axis in a second rotational direction opposite the first rotational direction results in a corresponding rotation of the cylindrical body in the second rotational direction, the exterior longitudinally oriented spiral groove converting rotational motion in the second rotational direction to linear motion to move the pushrod from the extended position to the retracted position.

A seal member may be made of an elastomer to form a seal between the distal end wall and a circumferential surface of the elongate needle.

The seal member may also form a seal between the distal end wall and a circumferential surface of the distal portion of the pushrod.

A safety insert may be positioned in the guide slot to prevent rotation of the actuator lever to until the safety insert is removed.

A marker loader may be configured to load the tissue marker into the marker recess in the second lumen of the elongate member. The marker loader may include a loader body having a mounting portion having a receptacle recess, and having a marker tube for carrying the tissue marker to be positioned in the marker recess in the second lumen of the elongate member. The receptacle recess of the mounting portion may be configured to be received over a distal end portion of the elongate member to align the marker tube with the second lumen of the elongate member. The marker loader may include a plunger having a head portion and a shaft portion. The shaft portion is slidably received in the marker tube. The plunger is configured to move between a holding position and a loaded position to deliver the tissue marker from the marker tube of the loader body to the marker recess in the second lumen of the elongate member.

The distal end portion of the elongate member may have an external figure-8 transverse shape, and the receptacle recess of the mounting portion of the loader body may have an internal figure-8 transverse shape to slidably receive the distal end portion of the elongate member in a snug fit.

A safety insert may be interposed between the head portion of the plunger and the loader body to prevent operation of the plunger of the marker loader to until the safety insert is removed.

A variation of the biopsy system described above may include an actuator mounted to the biopsy device. The actuator may be configured to be operable by a user to facilitate movement of the pushrod from the retracted position to the extended position to expel the tissue marker from the second lumen of the dual lumen coaxial introducer.

In this variation, the hub may include a hub body having a side wall, a proximal end wall, and a distal end wall. The side wall defines a hollow interior and an exterior surface, and has a latch slot that extends through the side wall from the exterior surface to the hollow interior. The proximal end wall has a first hole and a slotted hole. The distal end wall has a second hole. The first hole of the proximal end wall is configured to slidably receive the elongate needle and the second hole of the distal end wall is configured to receive and mount the proximal end portion of the elongate member. The slotted hole of the proximal end wall is configured to slidably receive the proximal portion of the pushrod.

The proximal end wall of the hub may be configured to define a spring seat. The pushrod has a proximal portion, a distal portion, and a flange interposed between the proximal portion and the distal portion. The distal portion is slidably received in the second lumen of the elongate member. A spring is positioned between the spring seat of the proximal end wall of the hub and the flange of the pushrod, wherein when the pushrod is in the retracted position, the spring is in a compressed state and when the pushrod is in the extended position, the spring is relaxed from the compressed state. An engagement member is positioned in the latch slot of the hub body to extend into the hollow interior of the hub body of the hub of the dual lumen coaxial introducer. The engagement member has a passage in which the pushrod movably resides. The engagement member defines a proximal engagement surface.

In this variation, the actuator has an actuator button and a linkage. The linkage is drivably interposed between the actuator button of the biopsy device and the proximal portion of the pushrod of the dual lumen coaxial introducer. When the pushrod is in the retracted position, the flange of the pushrod is engaged with the proximal engagement surface of the engagement member with the spring being in the compressed state. When a user applies an external force to the actuator button to move the actuator button, the movement of the actuator button effects a movement of the linkage to in turn laterally move the proximal end of the pushrod such that the flange of the pushrod is moved laterally out of engagement with the proximal engagement surface to release the spring from the compressed state to move the pushrod from the retracted position to the extended position.

A seal member may be positioned adjacent to the distal end wall in hollow interior of the hub body. The seal member has a third hole and a fourth hole. The first hole of the proximal end wall and the third hole of the seal member are aligned along the longitudinal axis and configured to slidably receive the elongate needle. The fourth hole is radially spaced from the third hole, with the pushrod slidably residing in the fourth hole.

As used herein, the term "dual lumen coaxial introducer" is an elongate structure in accordance with the present invention that has two lumen that are utilized as described herein, but the term does not preclude the elongate structure from having more than two lumen, wherein the additional lumen may be used for similar or additional purposes. Also, as used herein, the term "tissue marker" is used for convenience to represent a single tissue marker, or optionally, a group of tissue markers, for positioning in the marker recess of the marker lumen of the dual lumen coaxial introducer. The terms such as "first", "second", "third", etc., may be used for identification purposes and, in an identification context, are not to be limiting as to quantity, order, or importance, unless otherwise specified.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dual lumen coaxial introducer for use with an elongate needle of a medical device, comprising:
   a hub configured to releasably engage the medical device;
   an elongate member having a first lumen, a second lumen, a proximal end portion, and a distal end, the proximal end portion being fixedly attached to the hub, the first lumen defining a longitudinal axis and configured to slidably receive the elongate needle;

a pushrod located in the second lumen, the pushrod having a distal end surface, the pushrod being movable between a retracted position and an extended position, wherein in the retracted position, the distal end surface of the pushrod is spaced away from the distal end of the elongate member to define a marker recess in the second lumen for carrying a tissue marker for delivery to a delivery site; and an actuator mounted to the hub, the actuator configured to be operable by a user to facilitate movement of the pushrod from the retracted position to the extended position to expel the tissue marker from the second lumen, wherein the hub includes a hub body having a side wall, a proximal end wall, and a distal end wall, the side wall defining a hollow interior and an exterior surface, and having a guide channel that extends through the side wall from the exterior surface to the hollow interior, the proximal end wall having a first hole, and the distal end wall having a second hole, the first hole of the proximal end wall configured to slidably receive the elongate needle and the second hole of the distal end wall configured to receive and mount the proximal end portion of the elongate member.

2. The dual lumen coaxial introducer according to claim 1, comprising a seal member positioned adjacent to the distal end wall in the hollow interior of the hub body, the seal member having a third hole and a fourth hole, the first hole of the proximal end wall and the third hole of the seal member being aligned along the longitudinal axis and configured to slidably receive the elongate needle, the fourth hole being radially spaced from the third hole, the pushrod slidably residing in the fourth hole.

3. The dual lumen coaxial introducer according claim 2, wherein the seal member is made of an elastomer.

4. The dual lumen coaxial introducer according to claim 1, wherein:

the proximal end wall of the hub is configured to define a spring seat, and the pushrod has a proximal portion, a distal portion, and a flange interposed between the proximal portion and the distal portion, the distal portion being slidable within the second lumen of the elongate member, and further comprising:

a spring positioned between the spring seat of the proximal end wall of the hub and the flange of the pushrod, wherein when the pushrod is in the retracted position, the spring is in a compressed state and when the pushrod is in the extended position, the spring is relaxed from the compressed state; and the actuator configured as a button assembly having an actuator button attached to an engagement member, the engagement member having a passage in which the pushrod movably resides, the engagement member being positioned in the guide channel of the hub body to extend into the hollow interior of the hub body and the actuator button positioned to project outwardly from the guide channel, the engagement member having a proximal engagement surface, the actuator button configured to move the engagement member in the guide channel from an engaged position to a release position, wherein when the pushrod is in the retracted position and the engagement member of the actuator is in the engaged position, the flange of the pushrod is engaged with the proximal engagement surface of the engagement member with the spring being in the compressed state, and when the user applies an external force to the actuator button of the actuator to move the engagement member to the release position, the proximal engagement surface of the engagement member is moved out of the engaged position with the flange of the pushrod to release the spring from the compressed state to move the pushrod from the retracted position to the extended position.

5. The dual lumen coaxial introducer according to claim 4, wherein the external force depresses the actuator button of the actuator in a direction toward the pushrod.

6. The dual lumen coaxial introducer according to claim 1, further comprising a safety insert interposed between the actuator and the hub to prevent operation of the actuator until the safety insert is removed.

7. The dual lumen coaxial introducer according to claim 1, comprising a marker loader configured to load the tissue marker into the marker recess in the second lumen of the elongate member, the marker loader comprising:

a loader body having a mounting portion having a receptacle recess, and having a marker tube for carrying the tissue marker to be positioned in the marker recess in the second lumen of the elongate member, the receptacle recess of the mounting portion configured to be received over the distal end portion of the elongate member to align the marker tube of the loader body with the second lumen of the elongate member; and a plunger having a head portion and a shaft portion, the shaft portion being slidably received in the marker tube, the plunger configured to move between a holding position and a loaded position to deliver the tissue marker from the marker tube of the loader body to the marker recess in the second lumen of the elongate member.

8. The dual lumen coaxial introducer according to claim 7, wherein the distal end portion of the elongate member has an external Figure-8 transverse shape, and the receptacle recess of the mounting portion of the loader body has an internal Figure-8 transverse shape to slidably receive the distal end portion of the elongate member in a snug fit.

9. The dual lumen coaxial introducer according to claim 7, further comprising a safety insert interposed between the head portion of the plunger and the loader body to prevent operation of the plunger of the marker loader to until the safety insert is removed.

10. The dual lumen coaxial introducer according to claim 1, wherein the proximal end wall and the distal end wall of the hub are spaced apart along the longitudinal axis, and wherein the actuator further comprises an actuator lever that projects outwardly from the guide slot, the actuator lever being movable along the guide slot about the longitudinal axis.

11. The dual lumen coaxial introducer according to claim 10, wherein the pushrod has a proximal portion and a distal portion, the proximal portion having a drive protrusion, the distal portion being slidably received in the second lumen of the elongate member, and the actuator further including:

a cylindrical body drivably connected to the actuator lever, the cylindrical body having a cylindrical hole located on the longitudinal axis to slidably receive the elongate needle of the biopsy device, the cylindrical body having a proximal annular protrusion that defines a proximal bearing surface and a distal radial protrusion defining a second bearing surface, the first bearing surface and the second bearing surface being rotatably received in the hollow interior of the hub body, the cylindrical body having an exterior longitudinally oriented spiral groove, the exterior longitudinally oriented spiral groove configured to drivably receive the drive protrusion of the proximal portion of the pushrod, wherein a rotation of the actuator lever about the longitudinal axis in a first rotational direction results in a corresponding rotation of the cylindrical body in the first rotational direction, the exterior longitudinally oriented spiral groove converting rotational motion in the first rotational direction to linear motion to move the pushrod from the retracted position to the extended position, and wherein a rotation of the actuator lever about the longitudinal axis in a second rotational direction results in a corresponding rotation of the cylindrical body in the second rotational direction, the exterior longitudinally oriented spiral groove converting rotational motion in the second rotational direction to linear motion to move the pushrod from the extended position to the retracted position.

12. The dual lumen coaxial introducer according to claim 11, comprising a seal member made of an elastomer to form a seal between the distal end wall and a circumferential surface of the elongate needle.

13. The dual lumen coaxial introducer according to claim 12, the seal member also forming a seal between the distal end wall and a circumferential surface of the distal portion of the pushrod.

14. The dual lumen coaxial introducer according to claim 10, further comprising a safety insert positioned in the guide slot to prevent rotation of the actuator lever until the safety insert is removed.

15. The dual lumen coaxial introducer according to claim 10, comprising a marker loader configured to load the tissue marker into the marker recess in the second lumen of the elongate member, the marker loader comprising:

a loader body having a mounting portion having a receptacle recess, and having a marker tube for carrying the tissue marker to be positioned in the marker recess in the second lumen of the elongate member, the receptacle recess of the mounting portion configured to be received over a distal end portion of the elongate member to align the marker tube with the second lumen of the elongate member; and a plunger having a head portion and a shaft portion, the shaft portion being slidably received in the marker tube, the plunger configured to move between a holding position and a loaded position to deliver the tissue marker from the marker tube of the loader body to the marker recess in the second lumen of the elongate member.

16. The dual lumen coaxial introducer according to claim 15, wherein the distal end portion of the elongate member has an external Figure-8 transverse shape, and the receptacle recess of the mounting portion of the loader body has an internal Figure-8 transverse shape to slidably receive the distal end portion of the elongate member in a snug fit.

17. The dual lumen coaxial introducer according to claim 15, further comprising a safety insert interposed between the head portion of the plunger and the loader body to prevent operation of the plunger of the marker loader to until the safety insert is removed.

18. The dual lumen coaxial introducer according to claim 17, wherein the safety insert includes a channel that laterally slides over the shaft portion of the plunger.

* * * * *

UNITED STATES PATENT AND TRADEMARK OFFICE
CERTIFICATE OF CORRECTION

| | | |
|---|---|---|
| PATENT NO. | : 12,426,860 B2 | Page 1 of 1 |
| APPLICATION NO. | : 17/042533 | |
| DATED | : September 30, 2025 | |
| INVENTOR(S) | : Chad Van Liere, Angela K. Jensen and Channing M. Hughes | |

It is certified that error appears in the above-identified patent and that said Letters Patent is hereby corrected as shown below:

In the Claims

In Column 23, Line(s) 34, Claim 3, after "according", insert --to--.

In Column 24, Line(s) 45, Claim 9, after "loader", delete "to".

In Column 26, Line(s) 28, Claim 17, after "loader", delete "to".

Signed and Sealed this
Eighteenth Day of November, 2025

John A. Squires
*Director of the United States Patent and Trademark Office*